US012053277B2

(12) United States Patent
Huang et al.

(10) Patent No.: US 12,053,277 B2
(45) Date of Patent: Aug. 6, 2024

(54) INSERTION NEEDLE STRUCTURE AND INSERTER

(71) Applicant: BIONIME CORPORATION, Taichung (TW)

(72) Inventors: Li-Kang Huang, Taichung (TW); Chieh-Hsing Chen, Taichung (TW)

(73) Assignee: BIONIME CORPORATION, Taichung (TW)

( * ) Notice: Subject to any disclaimer, the term of this patent is extended or adjusted under 35 U.S.C. 154(b) by 483 days.

(21) Appl. No.: 17/450,834

(22) Filed: Oct. 14, 2021

(65) Prior Publication Data

US 2022/0110554 A1 Apr. 14, 2022

Related U.S. Application Data

(60) Provisional application No. 63/091,318, filed on Oct. 14, 2020.

(51) Int. Cl.
*A61B 5/145* (2006.01)
*A61B 5/00* (2006.01)

(52) U.S. Cl.
CPC ...... *A61B 5/14503* (2013.01); *A61B 5/14532* (2013.01); *A61B 5/6848* (2013.01)

(58) Field of Classification Search
CPC ............ A61B 5/14503; A61B 5/14532; A61B 5/6848; A61B 5/150374; A61B 5/150381; A61B 5/150389; A61B 5/150396; A61B 5/150404; A61B 5/150412; A61B 5/150442; A61B 5/150526; A61B 2560/063; A61B 5/14865; A61B 2017/3454; A61M 5/3286; B21G 1/08
See application file for complete search history.

(56) References Cited

U.S. PATENT DOCUMENTS 7,435,239 B2 * 10/2008 Yatabe ................ A61M 5/3286 604/272
9,597,461 B2 * 3/2017 Aasmul ............... A61M 5/3286
10,898,115 B2 1/2021 Halac et al.
10,932,709 B2 3/2021 Simpson et al.
11,648,032 B2 * 5/2023 Frey .................. A61M 37/0069 606/108

(Continued)

FOREIGN PATENT DOCUMENTS

EP 2195053 B1 6/2017
WO 2021025257 A1 2/2021
WO 2021025258 A1 2/2021

*Primary Examiner* — Eric J Messersmith

(74) *Attorney, Agent, or Firm* — CKC & Partners Co., LLC

(57) ABSTRACT

An insertion needle structure includes a needle sharp and a needle body. The needle body is integrally connected to the needle sharp and has a receiving space for receiving a biosensor. The needle body includes a base wall, two side walls and two slope sections. The side wall has a first inner edge and a first outer edge. The first inner edge is near the receiving space, and the first outer edge faces away from the receiving space. The slope section is connected between the side wall and the needle sharp. The slope section has a second inner edge connected to the first inner edge, and a second outer edge connected to the first outer edge. The first inner edge, the second inner edge, the first outer edge and the second outer edge are curved. A condition of R11>R12 is satisfied.

24 Claims, 25 Drawing Sheets

(56) References Cited

U.S. PATENT DOCUMENTS

| | | | | |
|---|---|---|---|---|
| 2004/0030302 | A1* | 2/2004 | Kamata | A61M 5/3286<br>604/272 |
| 2016/0361091 | A1* | 12/2016 | Frey | A61B 17/3421 |
| 2017/0188912 | A1* | 7/2017 | Halac | A61B 5/14532 |
| 2020/0077957 | A1* | 3/2020 | Akiyama | B21D 17/02 |
| 2020/0330014 | A1* | 10/2020 | Ueda | A61M 5/158 |
| 2021/0007651 | A1 | 1/2021 | Donnay et al. | |
| 2022/0047304 | A1* | 2/2022 | Akiyama | A61B 5/1473 |
| 2022/0322981 | A1* | 10/2022 | Chae | A61B 5/6849 |

* cited by examiner

INSERTION NEEDLE STRUCTURE AND INSERTER

RELATED APPLICATIONS

This application claims priority to U.S. Provisional Application Ser. No. 63/091,318, filed Oct. 14, 2020, which is herein incorporated by reference.

BACKGROUND

Technical Field

The present disclosure relates to an insertion needle and an inserter. Particularly, the present disclosure relates to an insertion needle and an inserter applied for inserting a biosensor.

Description of Related Art

Glucose monitor inside the body is very important for diabetes patients. In addition, the specific physiological parameters, such as blood fatty and the content of cholesterol, of the patients with the chronic illness have to be daily monitored for tracking the illness condition, thereby assisting the latter treatment. Generally, such physiological parameters are obtained by extracting the body fluid of the patient for further analysis, and, for example, a conventional glucose meter employs a needle to pierce the skin surface of the human body to extract the blood for analyzing the value of the glucose.

However, in order to improve the accuracy and immediacy of the monitor, a biosensor which can be implanted underneath the skin surface of the human body is developed. Through the biosensor, real-time physiological parameters can be obtained. The physiological parameters can be sent to the cloud or the back-end monitoring system in association with the signal processer, and numerous and immediate analyzed data can be provided, which prevents the discomfort and the risk of infection caused by invasive extractions of the body fluid.

The biosensor can be implanted underneath the skin surface of the human body by an inserter. The inserter can include an insertion needle, and the biosensor can be received in the insertion needle. By using the insertion needle to pierce the skin surface of the human body to form a small aperture, the biosensor can enter the aperture so as to be implanted underneath the skin surface of the human body. If the aperture is too large or non-smooth, the aperture, i.e., the wound, cannot heal quickly. Hence, how to improve the structure of the insertion needle to lower the burrs and increase the insertion smoothness for increasing the flatness of the aperture formed on the skin surface of the human body or the organism becomes a pursued target for practitioners.

SUMMARY

According to one aspect of the present disclosure, an insertion needle structure which is formed by bending a flat blank and is configured for receiving and allowing a biosensor to be partially implanted underneath a skin surface of an organism includes a needle sharp, a needle body and a reinforcing portion. The needle body is integrally connected to the needle sharp and has a receiving space for receiving the biosensor. The needle body includes a base wall, two side walls and two slope sections. The two side walls are located at two sides of the base wall, respectively. Each of the side walls has a first inner edge and a first outer edge. The first inner edge is near the receiving space, and the first outer edge faces away from the receiving space. The two slope sections are located at the two sides of the base wall, respectively. Each of the slope sections is connected between each of the side walls and the needle sharp, and each of the slope sections is curved. Each of the slope sections has a second inner edge connected to the first inner edge, and a second outer edge connected to the first outer edge. The reinforcing portion is disposed at at least one segment of a reinforcing area. The reinforcing area is defined as the needle sharp and a part of the needle body adjacent to the needle sharp. The reinforcing portion is constructed by forming at least one depression structure and/or at least one protrusion structure at the at least one segment to avoid the needle sharp from bending or deforming by a force during an implanting process. Each of the first inner edges, each of the second inner edges, each of the first outer edges and each of the second outer edges are curved. R11 represents a radius of each of the first inner edges, R12 represents a radius of each of the first outer edges, and a condition of R11>R12 is satisfied.

According to another aspect of the present disclosure, an insertion needle structure which is formed by bending a flat blank and is configured for receiving and allowing a biosensor to be partially implanted underneath a skin surface of an organism includes a needle sharp and a needle body. The needle body is integrally connected to the needle sharp and has a receiving space for receiving the biosensor. The needle body includes a base wall, two side walls and two slope sections. The two side walls are located at two sides of the base wall, respectively. Each of the side walls has a first inner edge and a first outer edge. The first inner edge is near the receiving space, and the first outer edge faces away from the receiving space. The two slope sections are located at the two sides of the base wall, respectively. Each of the slope sections is connected between each of the side walls and the needle sharp, and each of the slope sections is curved. Each of the slope sections has a second inner edge connected to the first inner edge, and a second outer edge connected to the first outer edge. Each of the first inner edges, each of the second inner edges, each of the first outer edges and each of the second outer edges are curved. R11 represents a radius of each of the first inner edges, R12 represents a radius of each of the first outer edges, and a condition of R11>R12 is satisfied.

According to yet another aspect of the present disclosure, an insertion needle structure which is formed by bending a flat blank and is configured for receiving and allowing a biosensor to be partially implanted underneath a skin surface of an organism includes a needle sharp and a needle body. The needle body is integrally connected to the needle sharp and has a receiving space for receiving the biosensor. The needle body includes a base wall, two side walls, and two slope sections. The two side walls are located at two sides of the base wall, respectively. Each of the side walls has a first inner edge and a first outer edge. The first inner edge is near the receiving space, and the first outer edge faces away from the receiving space. The two slope sections are located at the two sides of the base wall, respectively. Each of the slope sections is connected between each of the side walls and the needle sharp. Each of the slope sections has a second inner edge connected to the first inner edge, and a second outer edge connected to the first outer edge. Each of the first inner edges, each of the second inner edges, each of the first outer edges and each of the second outer edges are curved. R11 represents a radius of each of the first inner edges, R12 represents a radius of each of the first outer edges, and a condition of R11>R12 is satisfied.

According to still yet another aspect of the present disclosure, an inserter includes a cover having a main space, an inserting module disposed within the main space of the cover and including the abovementioned insertion needle structure, and a removing module including a base and a biosensor. The base is detachably limited within the inserting module. The biosensor is detachably assembled with the base and at least a part thereof is received in the receiving space of the insertion needle structure. When the cover is pressed downward, the inserting module is driven to allow the insertion needle structure to move downward so as to carry the biosensor to implant underneath the skin surface of the organism for conducting a measurement of a physiological signal inside the organism.

BRIEF DESCRIPTION OF THE DRAWINGS

The disclosure can be more fully understood by reading the following detailed description of the embodiments, with reference made to the accompanying drawings as follows.

DETAILED DESCRIPTION

It will be understood that when an element (or mechanism or module) is referred to as being "disposed on", "connected to" or "coupled to" another element, it can be directly disposed on, connected or coupled to another element, or it can be indirectly disposed on, connected or coupled to another element, that is, intervening elements may be present. In contrast, when an element is referred to as being "directly disposed on", "directly connected to" or "directly coupled to" another element, there are no intervening elements present.

In addition, the terms first, second, third, etc. are used herein to describe various elements or components, these elements or components should not be limited by these terms. Consequently, a first element or component discussed below could be termed a second element or component.

Figure 1:
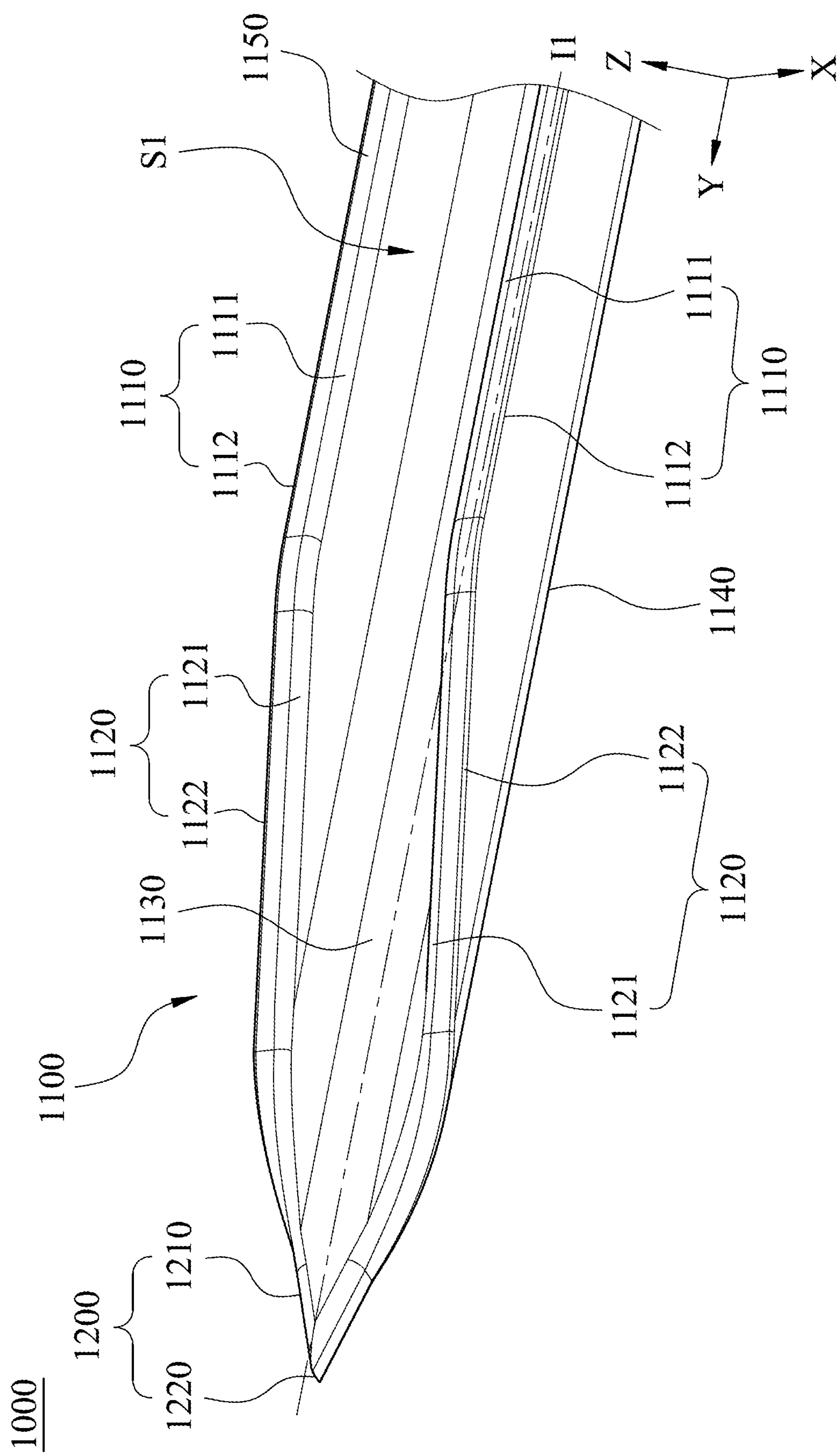
FIG. 1 shows a three-dimensional schematic view of an insertion needle structure according to a first embodiment of the present disclosure.
Figure 2:
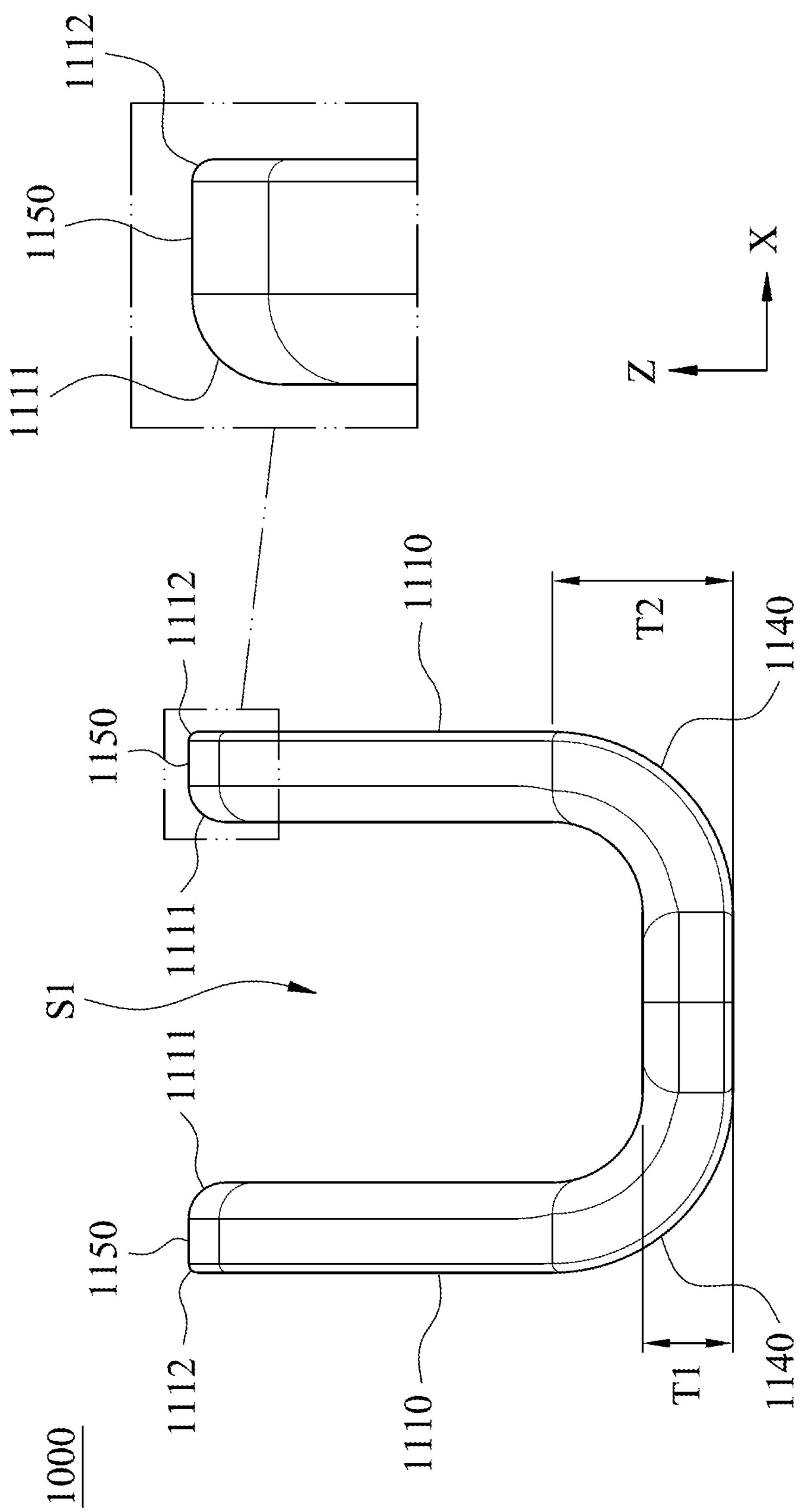
FIG. 2 shows a front view of the insertion needle structure of the first embodiment of FIG. 1.

FIG. 1 shows a three-dimensional schematic view of an insertion needle structure 1000 according to a first embodiment of the present disclosure. FIG. 2 shows a front view of the insertion needle structure 1000 of the first embodiment of FIG. 1. Please refer to FIGS. 1 and 2, the insertion needle structure 1000 which is formed by bending a flat blank B1 (shown in FIG. 5) and is configured for receiving and allowing a biosensor (not shown in the first embodiment) to be partially implanted underneath a skin surface (not shown) of an organism includes a needle sharp 1200 and a needle body 1100. The needle body 1100 is integrally connected to the needle sharp 1200 and includes a base wall 1130, two side walls 1110, and two slope sections 1120. A receiving space S1 for receiving the biosensor is defined by the two side walls 1110, the two slope sections 1120, and the base wall 1130. The two side walls 1110 are located at two sides of the base wall 1130, respectively. Each of the side walls 1110 has a first inner edge 1111 and a first outer edge 1112. The first inner edge 1111 is near the receiving space S1, and the first outer edge 1112 faces away from the receiving space S1. The two slope sections 1120 are located at the two sides of the base wall 1130, respectively. Each of the slope sections 1120 is connected between each of the side walls 1110 and the needle sharp 1200. Each of the slope sections 1120 has a second inner edge 1121 connected to the first inner edge 1111, and a second outer edge 1122 is connected to the first outer edge 1112. Each of the first inner edges 1111, each of the second inner edges 1121, each of the first outer edges 1112 and each of the second outer edges 1122 are curved. R11 represents a radius of each of the first inner edges 1111, R12 represents a radius of each of the first outer edges 1112, and a condition of R11>R12 is satisfied.

Therefore, because each of the first inner edges 1111, each of the second inner edges 1121, each of the first outer edges 1112 and each of the second outer edges 1122 are curved, the insertion needle structure 1000 is favorable for smoothly piercing the skin surface of the organism, which can increase the flatness of the aperture formed on the skin surface of the organism. Moreover, through the condition of R11>R12, damage of the biosensor inside the receiving space S1 can be avoided. The details of the insertion needle structure 1000 will be described hereinafter.

The insertion needle structure 1000 is a three-dimensional structure. Without considering the thickness, the base wall 1130 is located on a plane formed by a length direction Y and a width direction X of the insertion needle structure 1000, and the side walls 1110 and the slope sections 1120 are located on the plane formed by the length direction Y and a height direction Z of the insertion needle structure 1000. One of the side walls 1110 and one of the slope sections 1120 are located on one side of the central axis I1 of the insertion needle structure 1000, and the other one of the side walls 1110 and the other one of the slope sections 1120 are located on the other side of the central axis I1 of the insertion needle structure 1000. The two side walls 1110 are aligned symmetrically, and the two slope sections 1120 are aligned symmetrically.

The needle body 1100 can further include two curved connecting sections 1140, and each of the curved connecting sections 1140 is connected between each of the side walls 1110 and the base wall 1130 and between each of the slope sections 1120 and the base wall 1130. In other words, the base wall 1130 located on the plane formed by the length direction Y and the width direction X can be smoothly connected to the side walls 1110 and the slope sections 1120 on the plane formed by the length direction Y and the height direction Z so as to form a cross-section being U-shaped. Furthermore, each of the curved connecting sections 1140 has a height thereof represented by T2 along the height direction Z of the insertion needle structure 1000, the flat blank B1 has a thickness represented by T1 which is identical to the thickness of the base wall 1130 and is marked on FIG. 2, and a condition of T2/T1≥1.5 is satisfied. When the condition is satisfied, the anti-bending capability of the needle sharp 1200 can be increased to enhance the piercing capability, and the piercing force can be decreased to lower the piercing pain.

The needle body 1100 can further include a connecting surface 1150 which is parallel to the width direction X of the insertion needle structure 1000 and connected between each of the first inner edges 1111 and each of the first outer edges 1112. In other words, the inner surface and the outer surface of the side wall 1110 can be vertical. The radius angle of the first inner edge 1111 and the radius angle of the first outer edge 1112 are both 90 degrees, but the radius of the first inner edge 1111 and the radius of the first outer edge 1112 are different. As shown in the enlarged schematic view in FIG. 2, the first inner edge 1111 and the first outer edge 1112 are connected to each other via the connecting surface 1150. The second inner edge 1121 and the second outer edge 1122 can also be connected via the connecting surface 1150. The side wall 1110 can have a substantially uniform height which is defined by the distance from the intersection between the curved connecting section 1140 and the side wall 1110 to the connecting surface 1150 along the height direction Z. The height of the starting position of the slope section 1120 is substantially equal to zero, the height of the slope section 1120 is incrementally increased along the length direction Y, and the height of the stop position of the slope section 1120 is substantially equal to the height of the side wall 1110, thereby allowing the slope section 1120 to be smoothly connected to the side wall 1110. In the first embodiment, in addition to the starting position and the stop position, a slope of the height of the slope section 1120 is constant.

Figure 3:
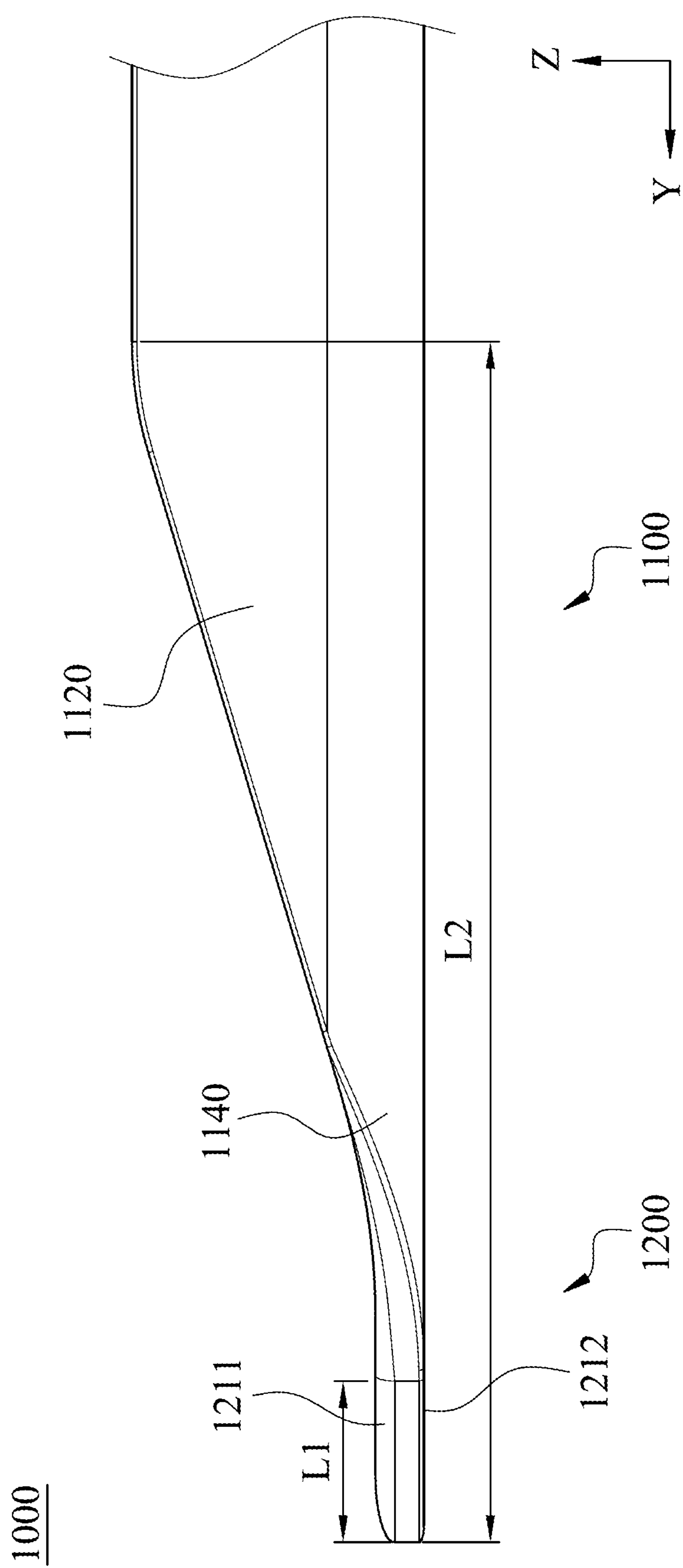
FIG. 3 shows a side view of the insertion needle structure of the first embodiment of FIG. 1.
Figure 4:
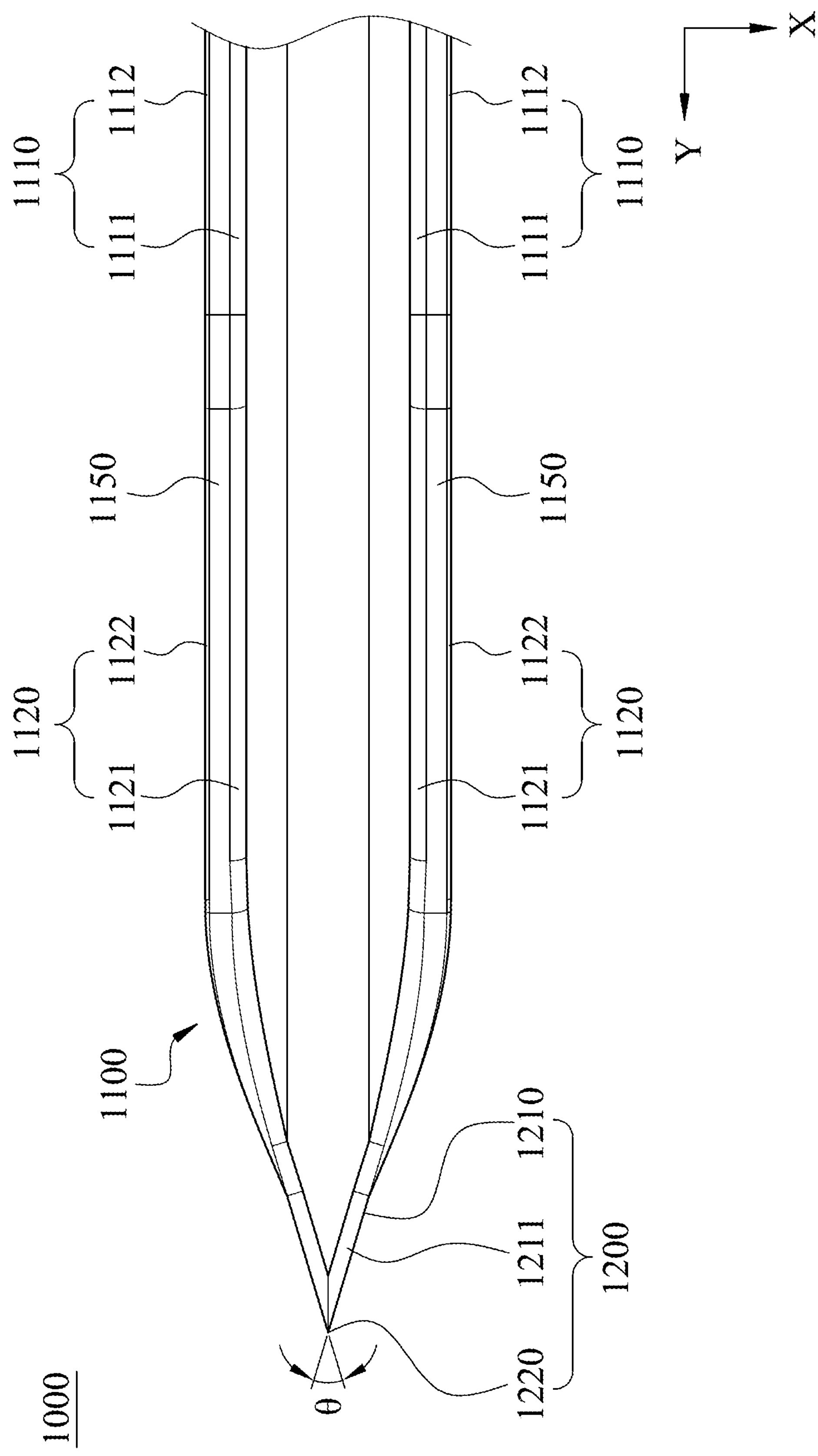
FIG. 4 shows a top view of the insertion needle structure of the first embodiment of FIG. 1.

FIG. 3 shows a side view of the insertion needle structure 1000 of the first embodiment of FIG. 1. FIG. 4 shows a top view of the insertion needle structure 1000 of the first embodiment of FIG. 1. Please refer to FIGS. 3 and 4 with reference to FIGS. 1 and 2. The needle sharp 1200 can include two slants 1210 connected to the two slope sections 1120, respectively, and the two slants 1210 intersect at a needle tip 1220 with an angle θ. Each of the slants 1210 includes a needle sharp top edge 1211 being curved and connected to one of the two second inner edges 1121, and a needle sharp bottom edge 1212 being curved and connected to one of the two second outer edges 1122. R31 represents a radius of each of the needle sharp top edges 1211, R32 represents a radius of each of the needle sharp bottom edges 1212, and a condition of R31>R32 is satisfied. Moreover, the angle θ is within a range from 20 degrees to 40 degrees.

To be more specific, the needle sharp 1200 is substantially triangle-shaped, and, without considering the thickness, the needle sharp 1200 is located at the plane formed by the length direction Y and the width direction X. Each of the slants 1210 is indirectly connected to the slope section 1120 via the curved connecting section 1140, and the needle tip 1220 is located at the central axis I1. Please be noted that, the curved connecting section 1140 is smoothly connected to the side wall 1110 and the slope section 1120, and therefore the height of the curved connecting section 1140 in the height direction Z is incrementally decreased toward the slant 1210 along the length direction Y. Each of the curved connecting sections 1140 can further include a third inner edge (not labeled) and a third outer edge (not labeled), each of the needle sharp top edges 1211 is indirectly connected to the second inner edge 1121 via the third inner edge, and each of the needle sharp bottom edges 1212 is indirectly connected to the second outer edge 1122 via the third outer edge.

Moreover, L1 represents a needle sharp length defined by a distance along the length direction Y between the needle tip 1220 and a stop position of each of the slants 1210, L2 represents an expanding length defined by a distance along the length direction Y between the needle tip 1220 and a stop position of each of the slope sections 1120, and a condition of L1/L2≤15% is satisfied. The stop position of each of the slants 1210 is defined as the intersection between the slant 1210 and the curved connecting section 1140. The stop position of the slope section 1120 is defined as the intersection between the slope section 1120 and the side wall 1110. As the condition of L1/L2≤15% is satisfied, particularly L1/L2≤8%, the smoothness for expanding the aperture formed by insertion of the needle sharp 1200 into the skin surface of the organism can be increased, thereby favorable for implanting the biosensor.

Figure 5:
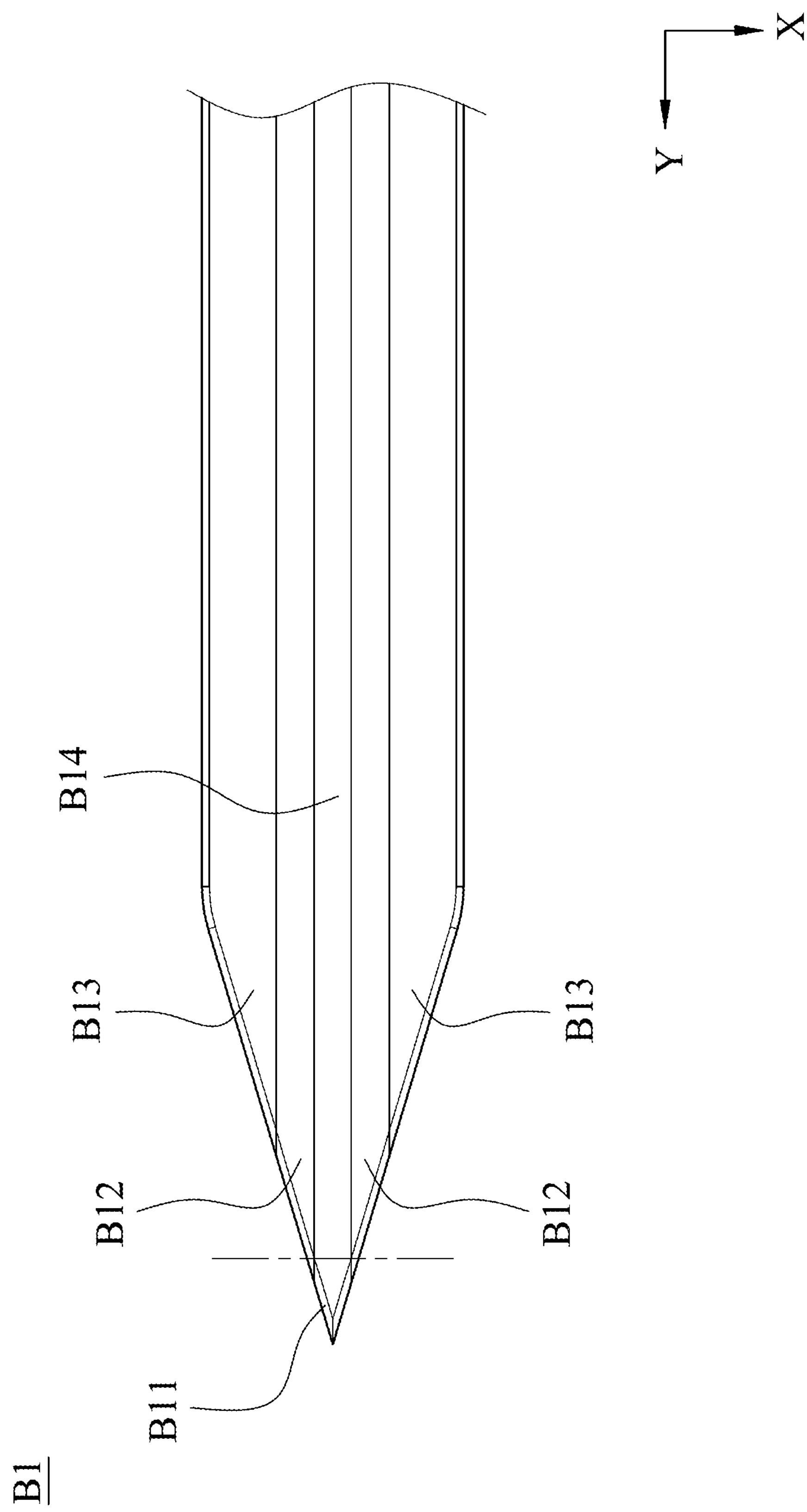
FIG. 5 shows a top view of a flat blank used for being bended and forming the insertion needle structure of the first embodiment of FIG. 1.

FIG. 5 shows a top view of a flat blank B1 used for being bended and forming the insertion needle structure 1000 of the first embodiment of FIG. 1. Please refer to FIG. 5 with reference to FIGS. 1 to 4, the flat blank B1 can be made of a metal board, and the flat blank B1 can be bended to form the insertion needle structure 1000. Consequently, the thickness T1 of the flat blank B1 is identical to the thickness of the base wall 1130, and is identical to the thickness of each of the side wall 1110, the slope sections 1120 and the curved connecting sections 1140. Moreover, through the configuration that the bending radius of the flat blank B1 is equal to the thickness T1, the curved connecting section 1140 with the height T2 can be formed.

The flat blank B1 can be formed by a stamping process, especially a cutting process. During the manufacture for forming the flat blank B1, a portion which is defined to form the needle sharp 1200, i.e., the needle sharp portion B11, is processed by the stamping mold, and then the area to be cut is continuously processed by the stamping mold for further process such as shaving to define the contour and to enhance the sharpness of the needle sharp 1200. As a result, a burr height formed as the flat blank B1 stamped from the sheet is smaller than or equal to 0.02 mm. A finishing surface can be formed as the flat blank B1 stamped from the sheet, the finishing surface has a depth represented by T3 (not shown), and the depth T3 of the finishing surface and the thickness T1 of the flat blank B1 satisfy a condition of $T3/T1 \geq 50\%$, particularly $T3/T1 \geq 70\%$, more particularly $T3/T1 \geq 90\%$. Through the manufacture process, the contour of the flat blank B1 can be a continuous and uniform cutting face, and the process for modifying the surface and reducing the burrs can be omitted.

In the first embodiment, the radius of each of the first inner edges 1111 is represented by R11, the radius of each of the second inner edges 1121 is represented by R21, and the radius of each of the needle sharp top edges 1211 is represented by R31. The radius of each of the first outer edges 1112 is represented by R12, the radius of each of the second outer edges 1122 is represented by R22, and the radius of each of the needle sharp bottom edges 1212 is represented by R32. Conditions of $R11=R21=R31$ and $R12=R22=R32$ are satisfied. Moreover, each of the first outer edges 1112, each of the second outer edges 1122 and each of the needle sharp bottom edges 1212 are formed as the flat blank B1 stamped and elastic deformed from the sheet. Precisely, during stamping, the area to be cut will first be elastic deformed, then be plastically deformed, and finally be torn off. Therefore, the flat blank B1 which is completely separated from the sheet can be formed. As viewing from the side, a rollover zone and the rest, which is represented by a shear zone, caused by stamping the flat blank B1 can be formed. The rollover zone is curved owing to the elastic deformation, and can be used as the first outer edges 1112, the second outer edges 1122 and the needle sharp bottom edges 1212 without further processes. Consequently, the condition of $20\% \leq R11/T1 \leq 50\%$ can be satisfied. The shear zone is caused by plastic deformation, and the finishing surface is originally about 30% to 50% of the thickness T1 of the flat blank B1. The present disclosure can use the stamping mold and the process such as the shaving to increase the depth of the finishing surface to about more than 50% of the thickness T1 or about more than 70% of the thickness T1. Additionally, at least a part of the remained burrs can be rounded to form the first inner edges 1111, the second inner edges 1121 and the needle sharp top edges 1211, and a condition of $3 \leq R11/R12 \leq 10$ can be satisfied. As a result, the flat area of the cutting face of the flat blank B1 can be decreased and the remained small burrs can be removed. The friction between the insertion needle structure 1000 bended therefrom and the skin surface of the organism can be lowered during the inserting process.

The flat blank B1 can include a needle sharp portion B11, a base wall portion B14, two radius angle portions B12 and two wing portions B13. The needle sharp portion B11 is substantially triangle-shaped, and the base wall portion B14 can be strip-shaped and can be integrally connected to the needle sharp portion B11. A width of the base wall portion B14 is equal to the maximum width of the needle sharp portion B11. Each of the radius angle portions B12 is integrally connected to the base wall portion B14 and has an inclined line extending from the needle sharp portion B11. Each of the wing portions B13 is integrally connected to the radius angle portion B12 and has an inclined line extending from the radius angle portion B12, which has the same slope of the inclined line extending from the needle sharp portion B11, and a straight line connected to the inclined line. After the flat blank B1 is bended, the needle sharp portion B11 forms the needle sharp 1200, the radius angle portion B12 forms the curved connecting section 1140, and the wing portion B13 forms the side wall 1110 and the slope section 1120, thereby completing the insertion needle structure 1000.

Figure 6:
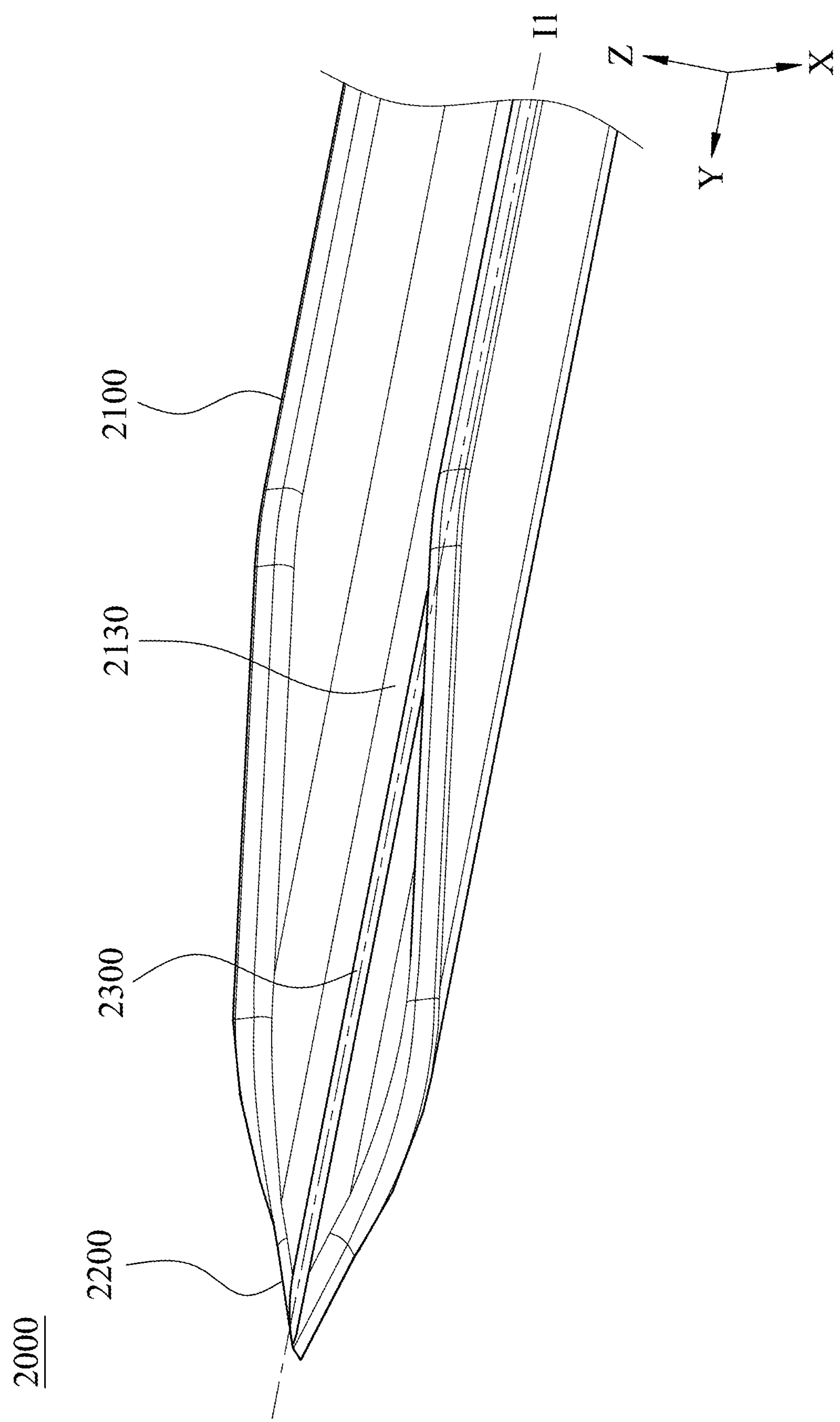
FIG. 6 shows one three-dimensional schematic view of an insertion needle structure according to a second embodiment of the present disclosure.
Figure 7:
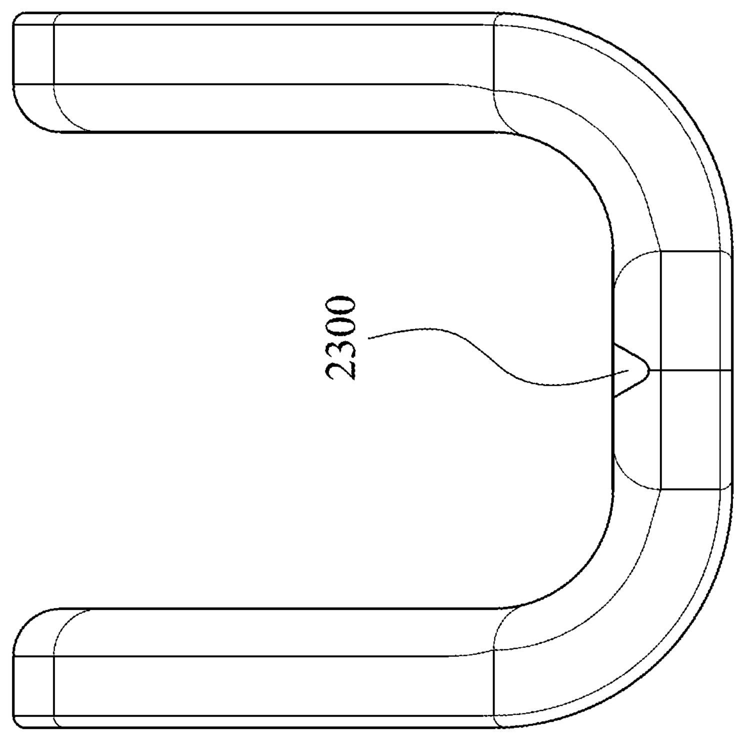
FIG. 7 shows a front view of the insertion needle structure of the second embodiment of FIG. 6.
Figure 8:
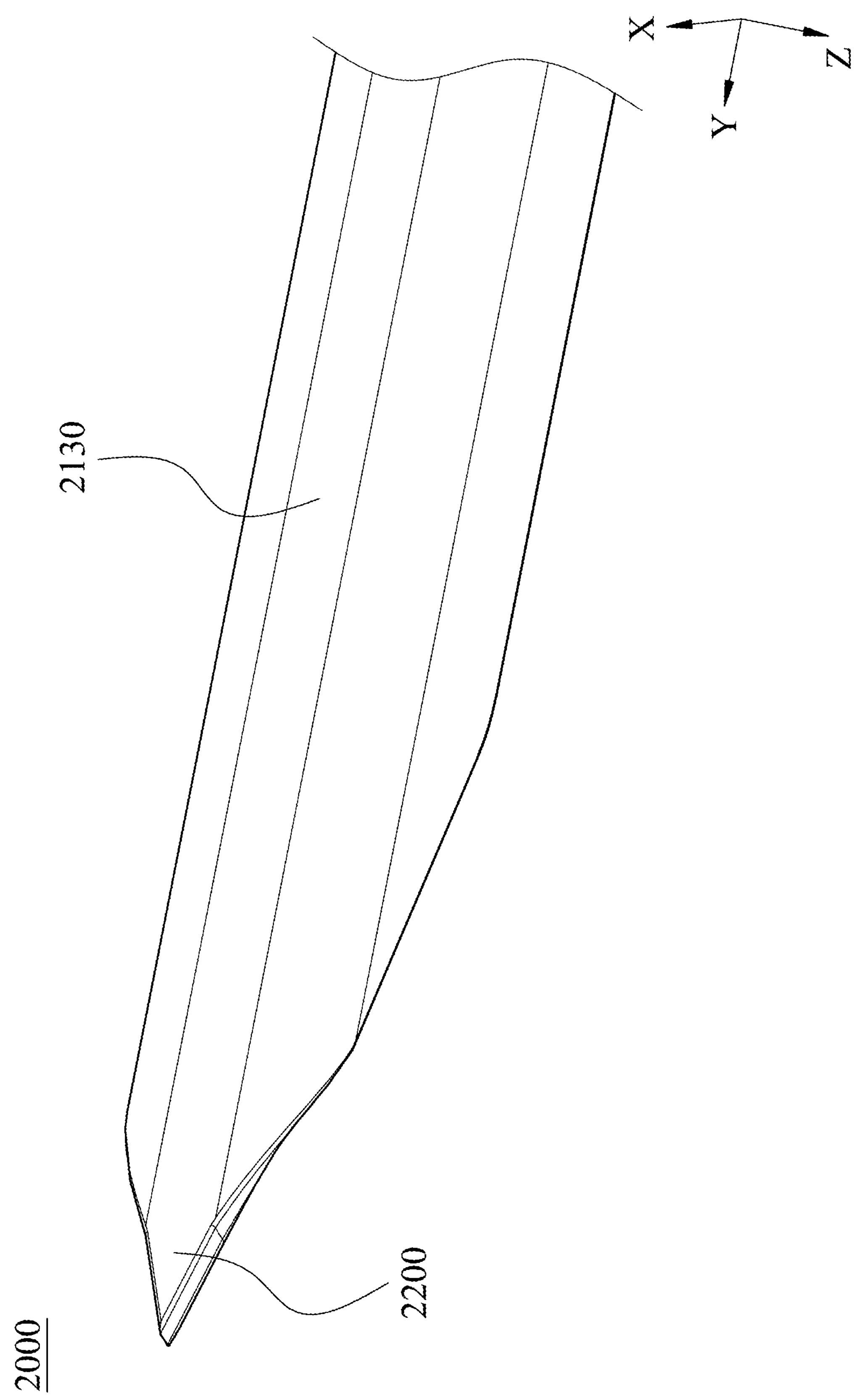
FIG. 8 shows another three-dimensional schematic view of the insertion needle structure of the second embodiment of FIG. 6.

FIG. 6 shows one three-dimensional schematic view of an insertion needle structure 2000 according to a second embodiment of the present disclosure. FIG. 7 shows a front view of the insertion needle structure 2000 of the second embodiment of FIG. 6. FIG. 8 shows another three-dimensional schematic view of the insertion needle structure 2000 of the second embodiment of FIG. 6. The insertion needle structure 2000 is similar to the insertion needle structure 1000 of the first embodiment and includes a needle sharp 2200 and a needle body 2100. The difference is that the insertion needle structure 2000 can further include a reinforcing portion (not labeled). The reinforcing portion is disposed at at least one of the needle sharp 2200 and the needle body 2100 along the length direction Y. Particularly, a reinforcing area is defined as the needle sharp 2200 and a part of the needle body 2100 adjacent to the needle sharp 2200. The reinforcing portion is disposed at at least one segment of a reinforcing area. The reinforcing portion is constructed by forming at least one depression structure and/or at least one protrusion structure at the at least one segment. As shown in FIGS. 6 to 8, the reinforcing portion includes a groove 2300, and the groove 2300 extends from the needle sharp 2200 toward the base wall 2130 of the needle body 2100. The groove 2300 can be located at a first surface of the needle sharp 2200 facing toward the receiving space (not labeled in the second embodiment) and at a first surface of the base wall 2130 facing toward the receiving space, and the groove 2300 can be positioned at the central axis I1. During the manufacture, the groove 2300 can be formed on the needle sharp portion (not shown in the second embodiment) and the base wall part (not shown in the second embodiment) of the flat blank (not shown in the second embodiment) first, and the depth of the groove 2300 is not larger than or equal to the thickness of the flat blank. The insertion needle structure 2000 having the groove 2300 can then be formed by bending the flat blank, and a second surface of the needle sharp 2200 facing away from the receiving space and a second surface of the base wall 2130 facing away from the receiving space are still smooth surfaces. Precisely, the groove 2300 is formed by pressing the first surface of the needle sharp portion and the first surface of the base wall portion. Please be noted that, during the manufacture, the groove 2300 extends no further than the part of the base wall portion adjacent to the needle sharp portion. The material density of the needle sharp 2200 will be increased after pressing, and the strength of the needle sharp 2200 can be enhanced, thereby favorable for increasing the anti-bending capability of the insertion needle structure 2000 and avoiding the needle sharp 2200 from bending or deforming during the implanting process. In other embodiments, the groove can also be formed by cutting off a part of the material. The reinforcing portion can include a plurality of grooves, the reinforcing portion can only be located on the needle sharp, and the present disclosure is not limited thereto.

Figure 9:
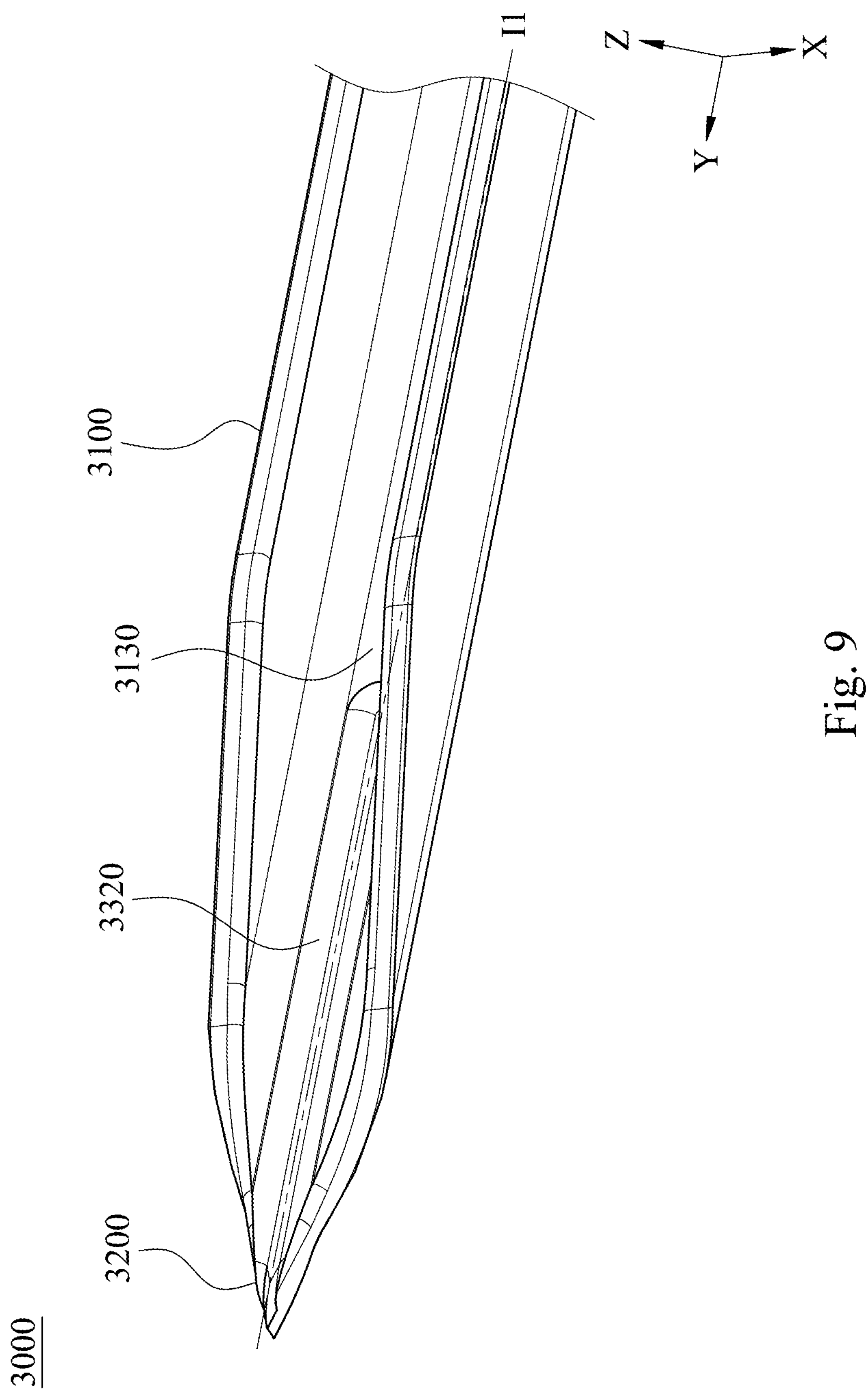
FIG. 9 shows one three-dimensional schematic view of an insertion needle structure according to a third embodiment of the present disclosure.
Figure 10:
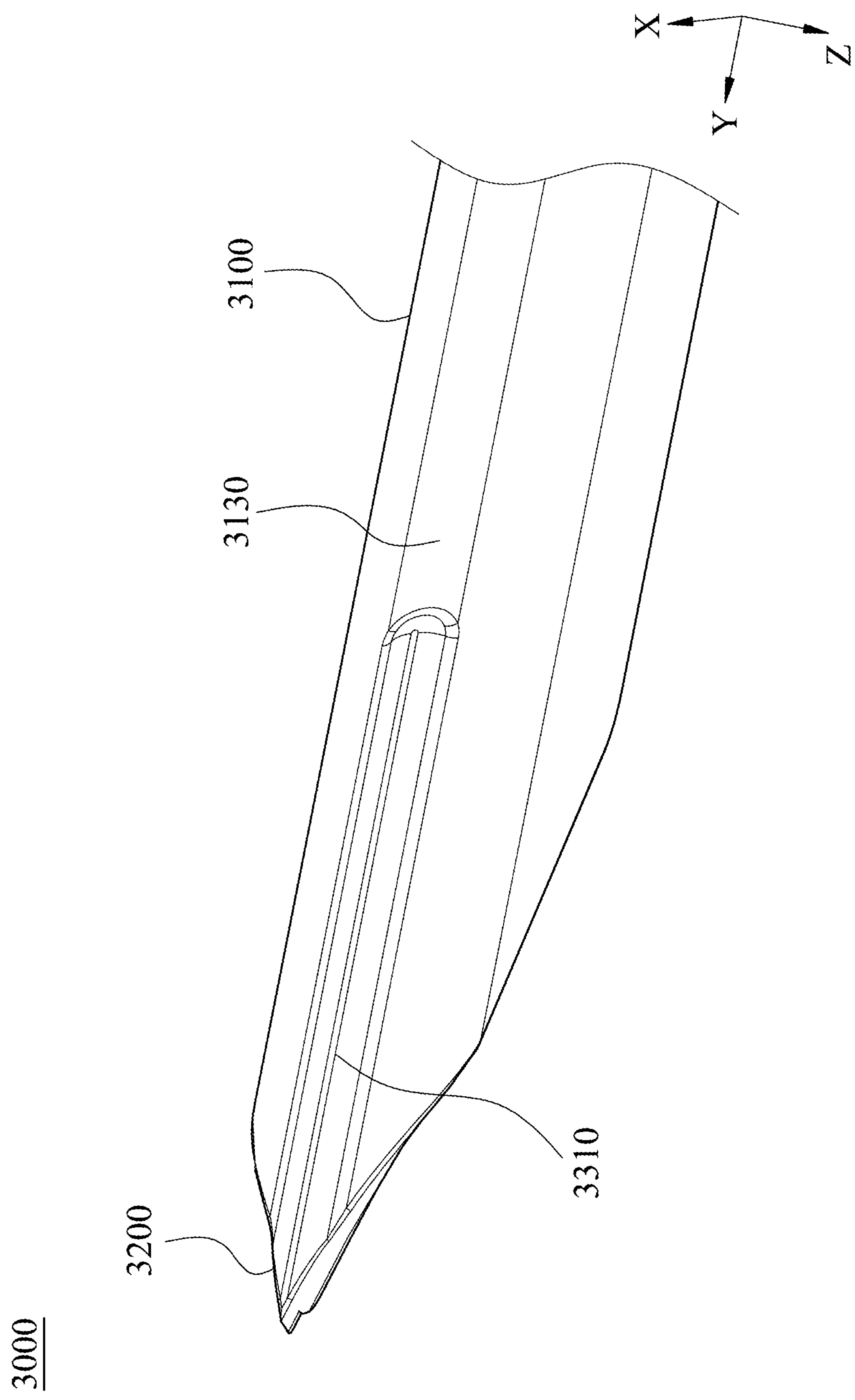
FIG. 10 shows another three-dimensional schematic view of the insertion needle structure of the third embodiment of FIG. 9.
Figure 11:
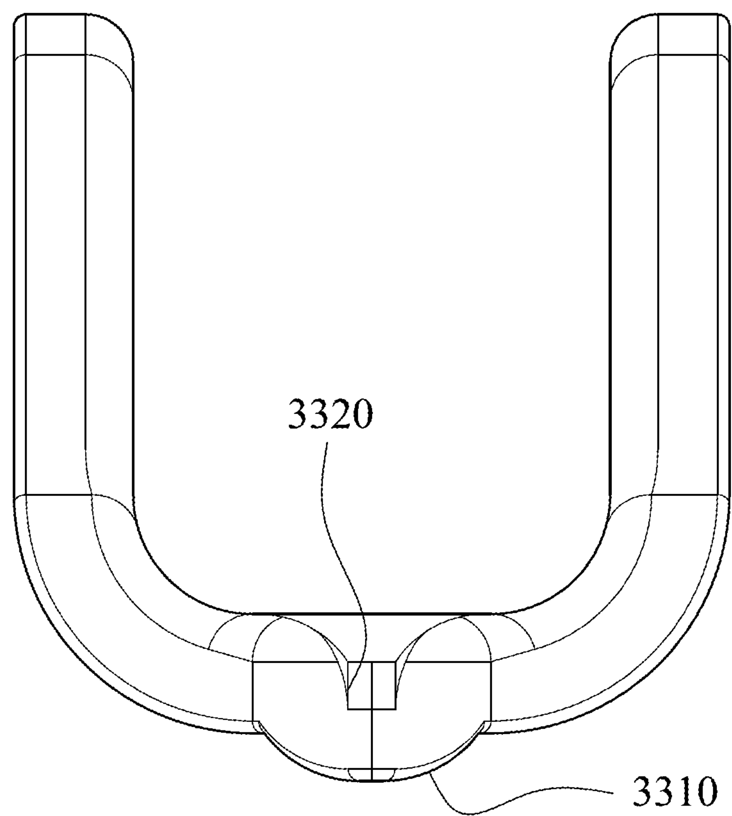
FIG. 11 shows a front view of the insertion needle structure of the third embodiment of FIG. 9.
Figure 12:
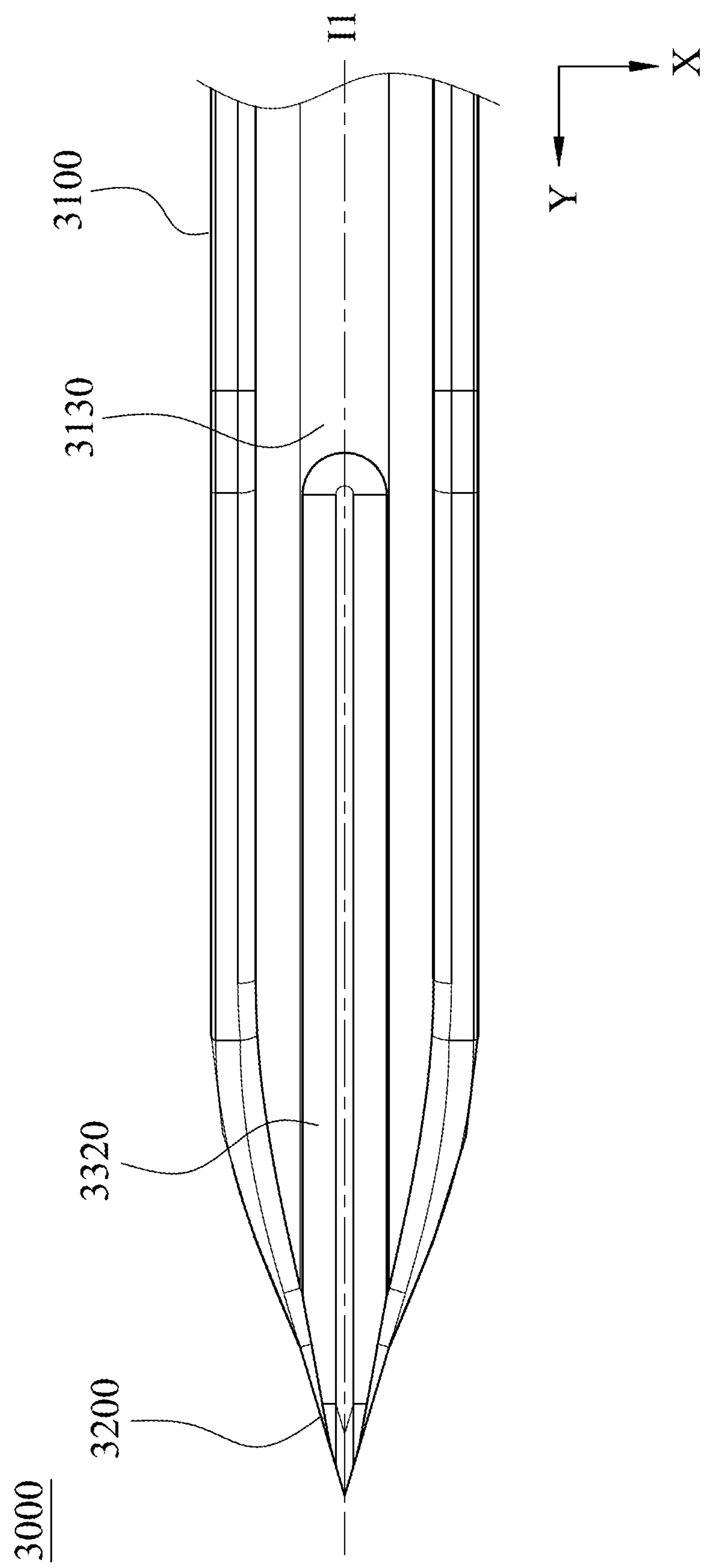
FIG. 12 shows a top view of the insertion needle structure of the third embodiment of FIG. 9.
Figure 13:
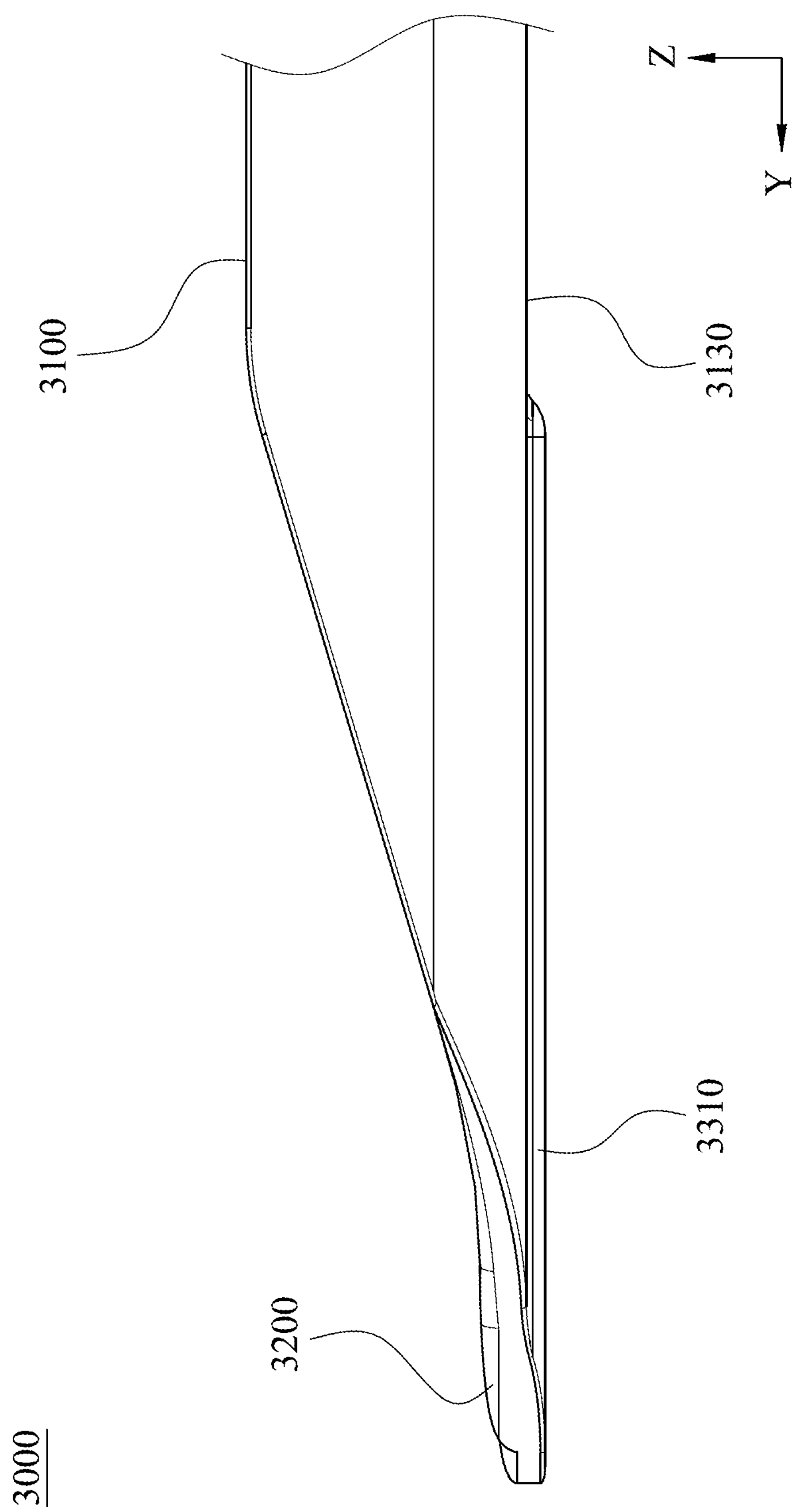
FIG. 13 shows a side view of the insertion needle structure of the third embodiment of FIG. 9.

FIG. 9 shows one three-dimensional schematic view of an insertion needle structure 3000 according to a third embodiment of the present disclosure. FIG. 10 shows another three-dimensional schematic view of the insertion needle structure 3000 of the third embodiment of FIG. 9. FIG. 11 shows a front view of the insertion needle structure 3000 of the third embodiment of FIG. 9. FIG. 12 shows a top view of the insertion needle structure 3000 of the third embodiment of FIG. 9. FIG. 13 shows a side view of the insertion needle structure 3000 of the third embodiment of FIG. 9. The insertion needle structure 3000 is similar to the insertion needle structure 1000 of the first embodiment and includes a needle sharp 3200 and a needle body 3100. The difference is that the insertion needle structure 3000 can further include a reinforcing portion (not labeled). The reinforcing portion includes a rib 3310, and the rib 3310 extends from the needle sharp 3200 toward the base wall 3130 of the needle body 3100. To be more specific, the reinforcing portion can further include a pressed depression 3320, the pressed depression 3320 can be located at a first surface of the needle sharp 3200 facing toward the receiving space (not labeled in the third embodiment) and at a first surface of the base wall 3130 facing toward the receiving space, and the pressed depression 3320 can be positioned at the central axis I1. The rib 3310 is located at a second surface of the needle sharp 3200 facing away from the receiving space and at a second surface of the base wall 3130 facing away from the receiving space, and the rib 3310 can be positioned at the central axis I1. In other words, the pressed depression 3320 and the rib 3310 correspond to each other. During the manufacture, the pressed depression 3320 can be formed on the first surfaces of the needle sharp portion (not shown in the third embodiment) and the base wall part (not shown in the third embodiment) of the flat blank (not shown in the third embodiment) first, and the depth of the pressed depression 3320 is larger than the thickness of the flat blank, thereby automatically forming the rib 3310 protruding from the second surface. The insertion needle structure 3000 having the pressed depression 3320 and the rib 3310 can then be formed by bending the flat blank. Please be noted that, during the manufacture, the pressed depression 3320 extends no further than the part of the base wall portion adjacent to the needle sharp portion, and the rib 3310 extends no further than the part of the base wall portion adjacent to the needle sharp portion correspondingly. In the third embodiment, the pressed depression 3320 is pressed by the same pressing method, and the protruding rib 3310 which is thinner and has higher material density can be formed. Hence, the material density of the needle sharp 3200 will be increased after pressing, and the strength of the needle sharp 3200 can be enhanced, thereby favorable for increasing the anti-bending capability of the insertion needle structure 3000. The manufacturing process of the present disclosure is not limited thereto. Moreover, the reinforcing portion is not limited to the groove, e.g., the groove 2300 in the second embodiment, or the rib, e.g., the rib 3310 in the third embodiment, the reinforcing portion can be a projection protruding from the second surface of the needle sharp facing away from the receiving space, and the reinforcing portion can be only disposed at the needle sharp.

Figure 14:
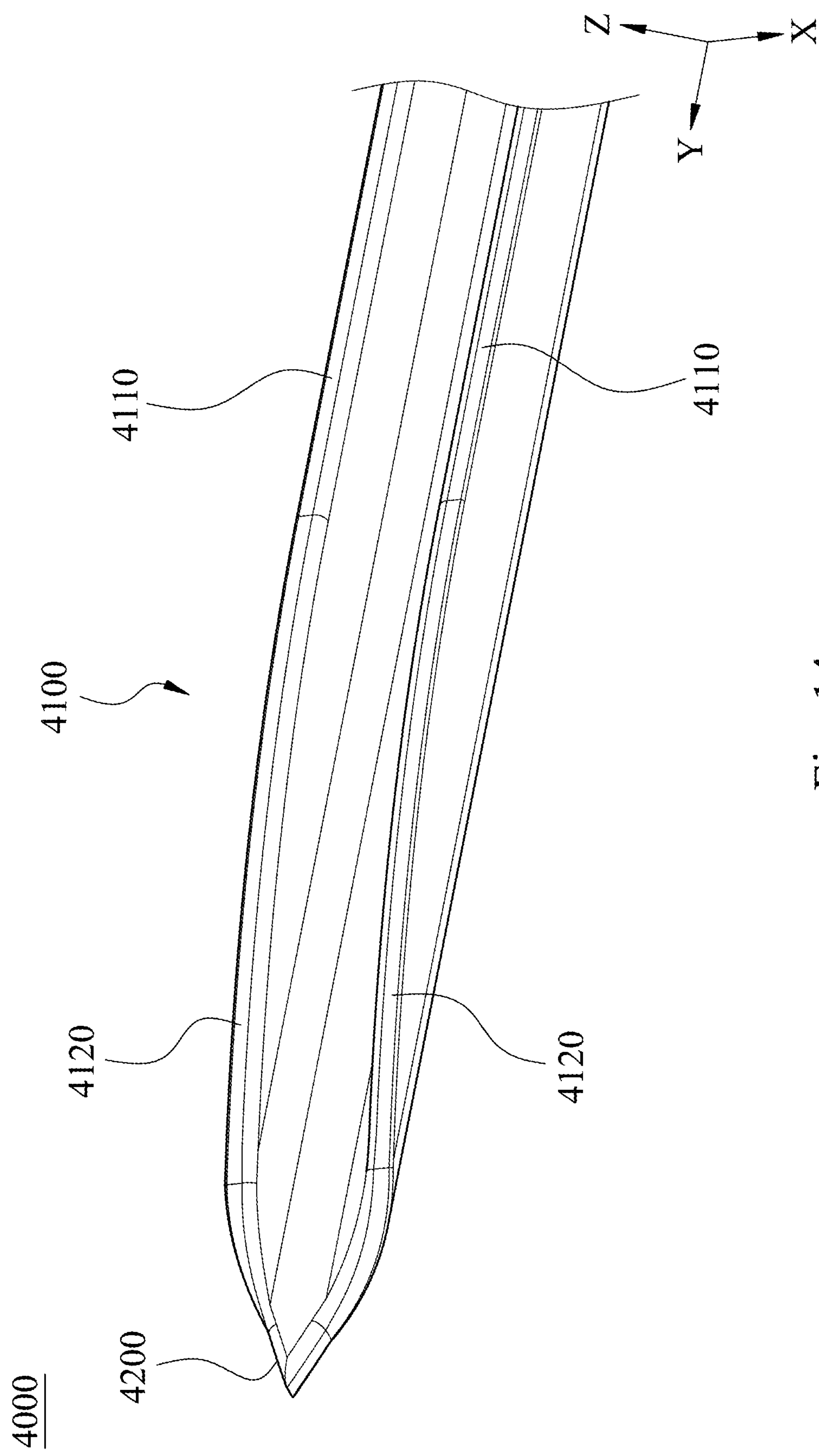
FIG. 14 shows a three-dimensional schematic view of an insertion needle structure according to a fourth embodiment of the present disclosure.
Figure 15:
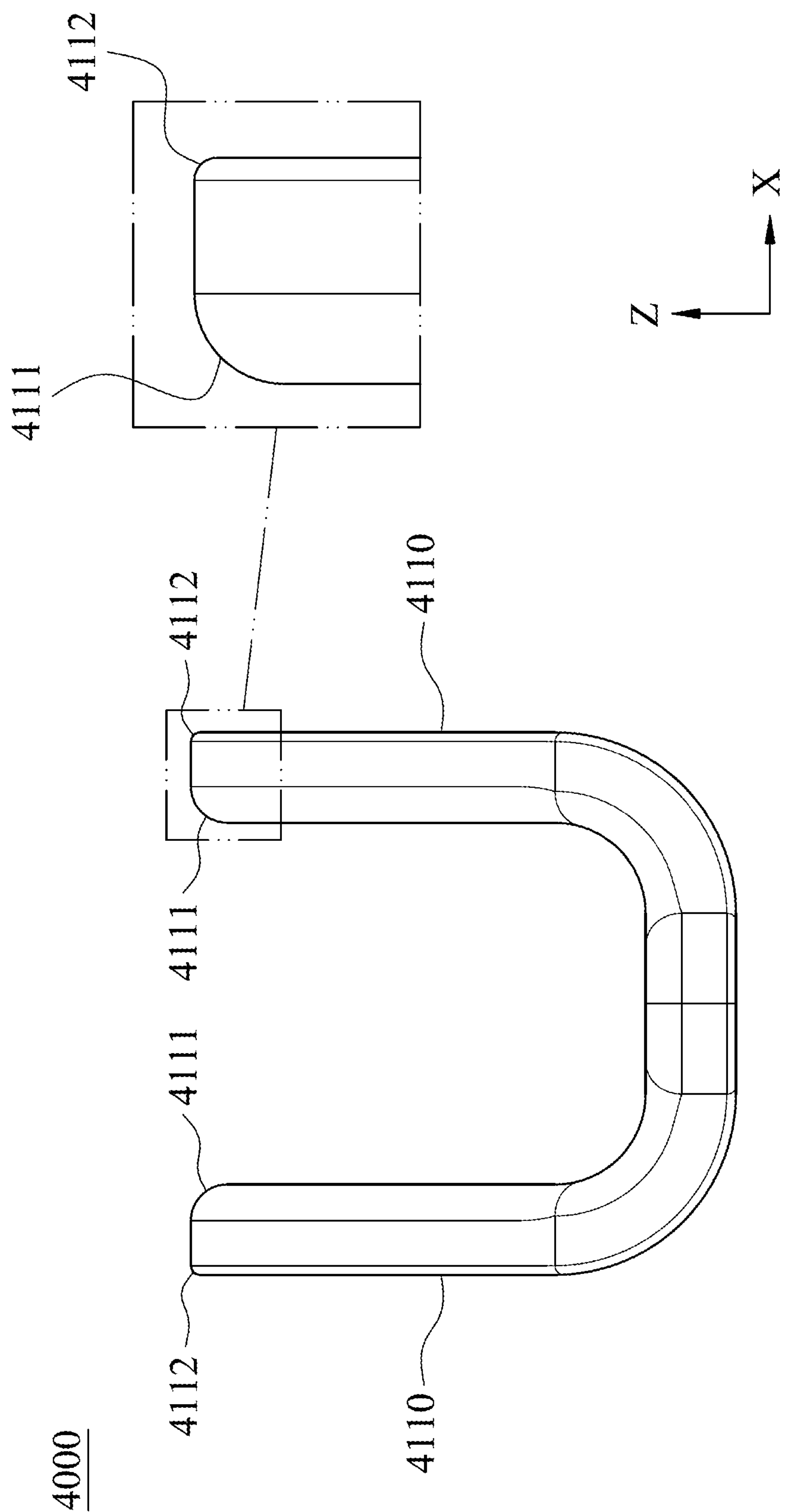
FIG. 15 shows a front view of the insertion needle structure of the fourth embodiment of FIG. 14.
Figure 16:
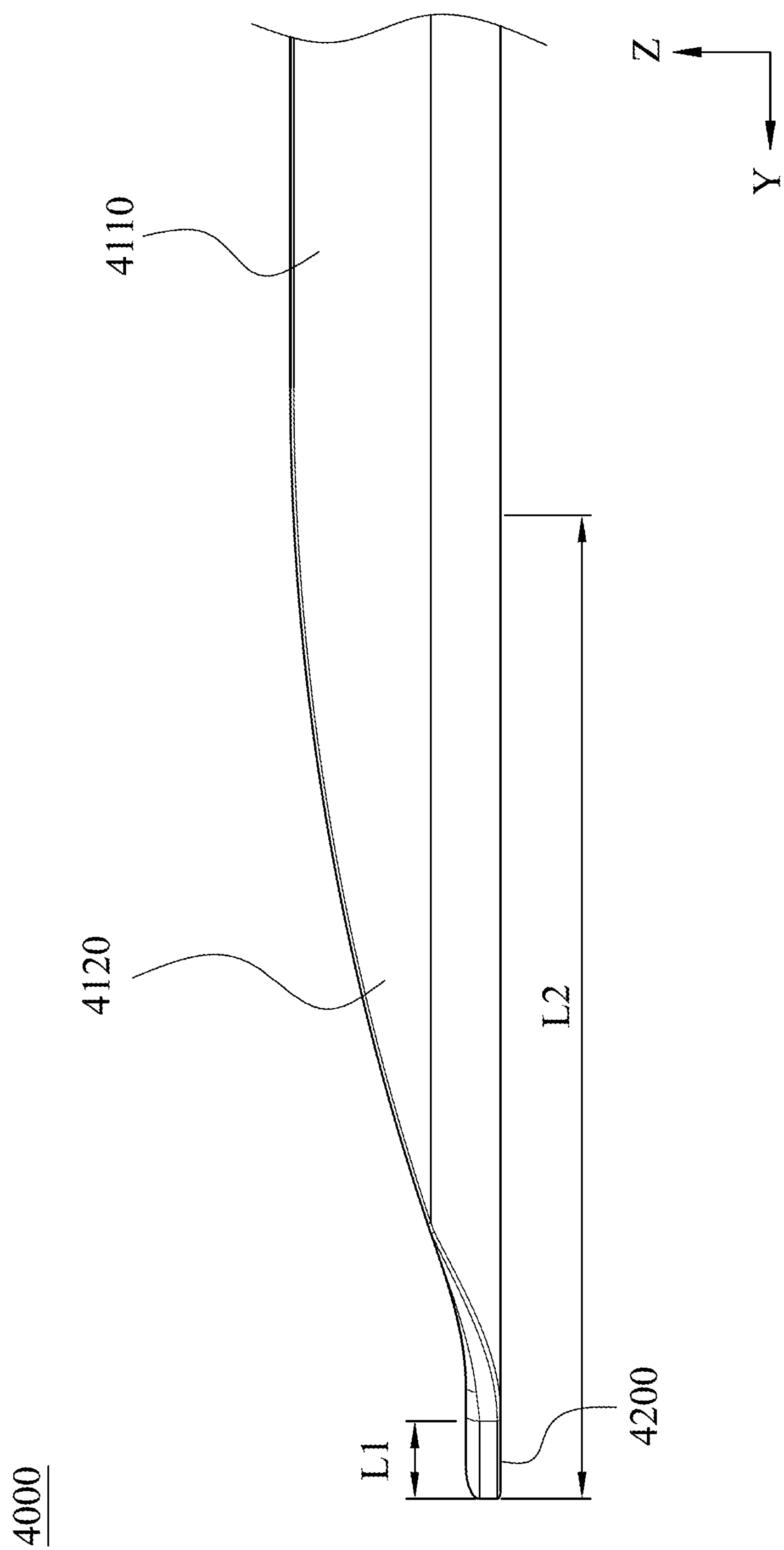
FIG. 16 shows a side view of the insertion needle structure of the fourth embodiment of FIG. 14.

FIG. 14 shows a three-dimensional schematic view of an insertion needle structure 4000 according to a fourth embodiment of the present disclosure. FIG. 15 shows a front view of the insertion needle structure 4000 of the fourth embodiment of FIG. 14. FIG. 16 shows a side view of the insertion needle structure 4000 of the fourth embodiment of FIG. 14. The insertion needle structure 4000 is similar to the insertion needle structure 1000 and includes a needle sharp 4200 and a needle body 4100. The needle body 4100 includes two slope sections 4120 and two side walls 4110, and each of the side walls 4110 includes a first inner edge 4111 and a first outer edge 4112. The difference is that each of the slope sections 4120 is curved. In other words, the front end of the needle body 4100 of the insertion needle structure 4000 in the fourth embodiment connected to the needle sharp 4200 is curved. More particularly, a projected line generated by projecting the height of each of the slope sections 4120 onto the plane formed by the height direction Z and the length direction Y is a curved line with its convex vertex facing upward. The tangent slopes of different height positions of the slope section 4120 are different.

Figure 17:
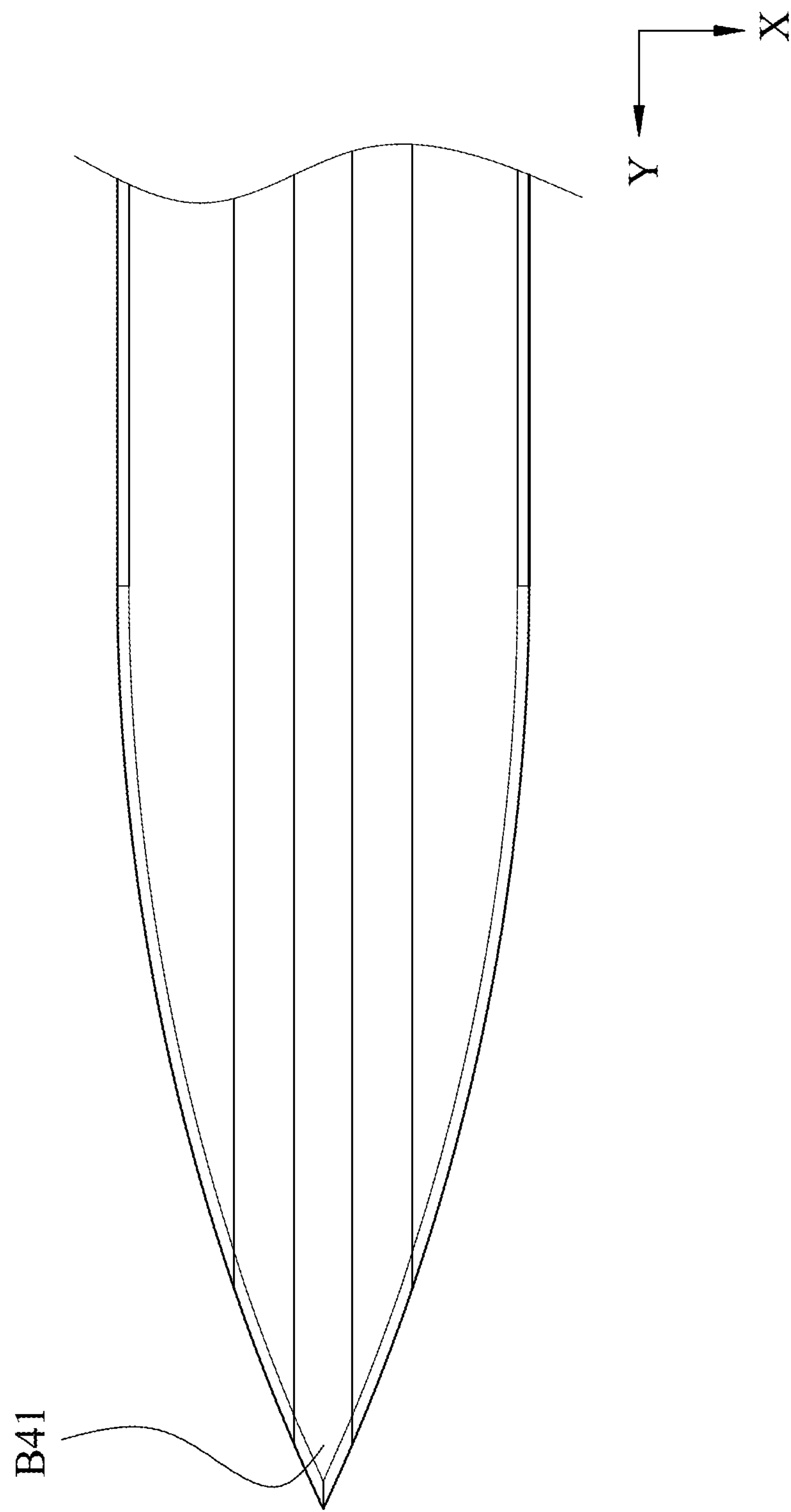
FIG. 17 shows a top view of a flat blank used for being bended and forming the insertion needle structure of the fourth embodiment of FIG. 14.

FIG. 17 shows a top view of a flat blank B4 used for being bended and forming the insertion needle structure 4000 of the fourth embodiment of FIG. 14. Please refer to FIG. 17 with reference to FIGS. 14 to 16, the flat blank B4 is used for being bended and forming the insertion needle structure 4000. The flat blank B4 is similar to the flat blank B1 of the first embodiment. The difference is that the inclined line extending from the needle sharp portion B41 is curved, and no obvious inflection point is presented at the intersection between the inclined line and the straight line. Therefore, the needle sharp 4200 of the insertion needle structure 4000 is shortened while the width thereof is increased, thereby increasing the structural strength of the needle sharp 4200 to avoid bending of the needle sharp 4200. Moreover, through the curved slope sections 4120, the aperture formed by piercing the skin surface of the organism can be smoothly expanded, and the smoothness of the implanting process can be increased. As a result, the piercing pain can be lowered, which facilitates for implanting the biosensor. In other embodiments, the curve of each of the slope sections can be increased, but the sharpness should be taken into consideration while modifying the curve of each of the slope sections.

Figure 18:
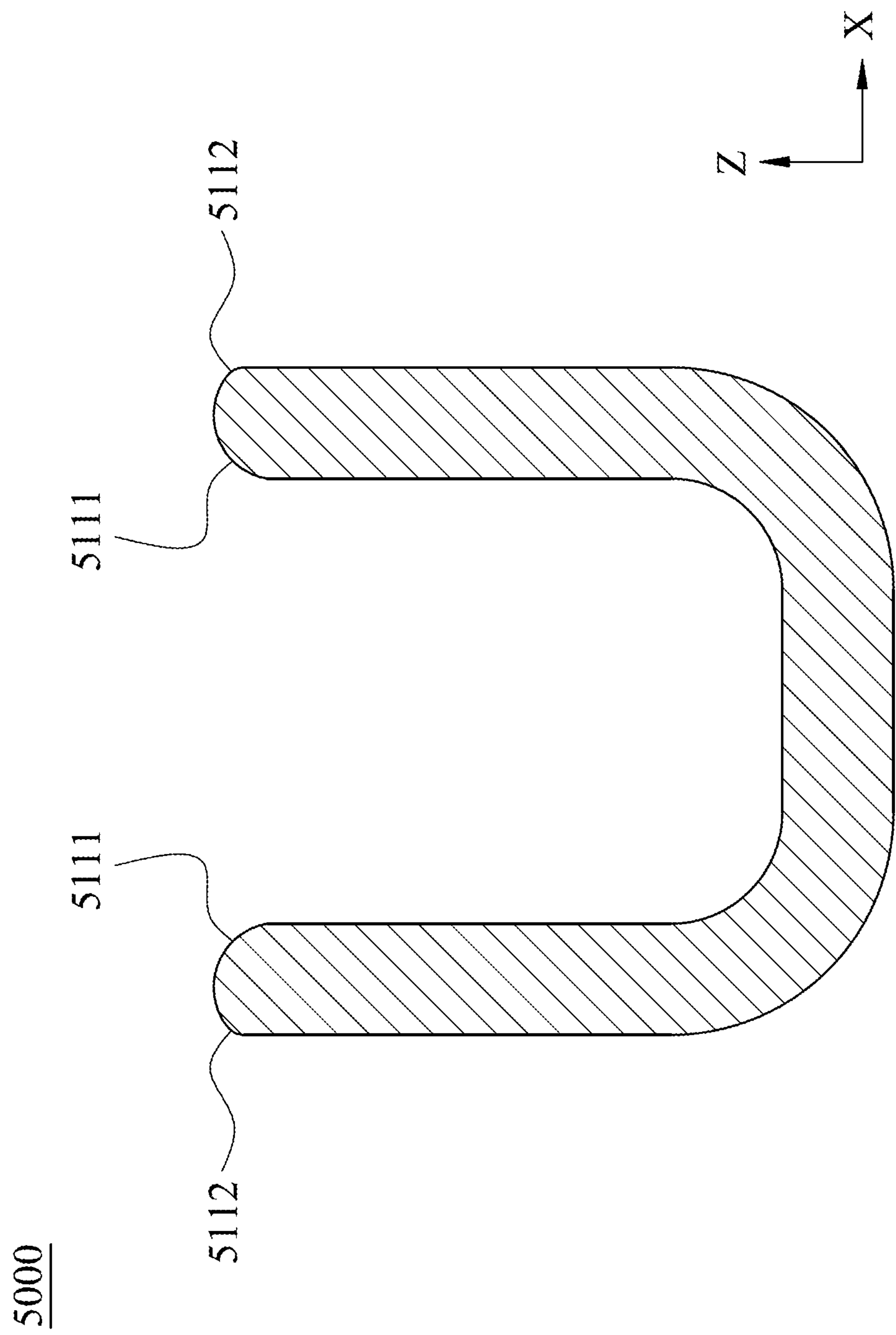
FIG. 18 shows a front section view of an insertion needle structure according to a fifth embodiment of the present disclosure.
Figure 19:
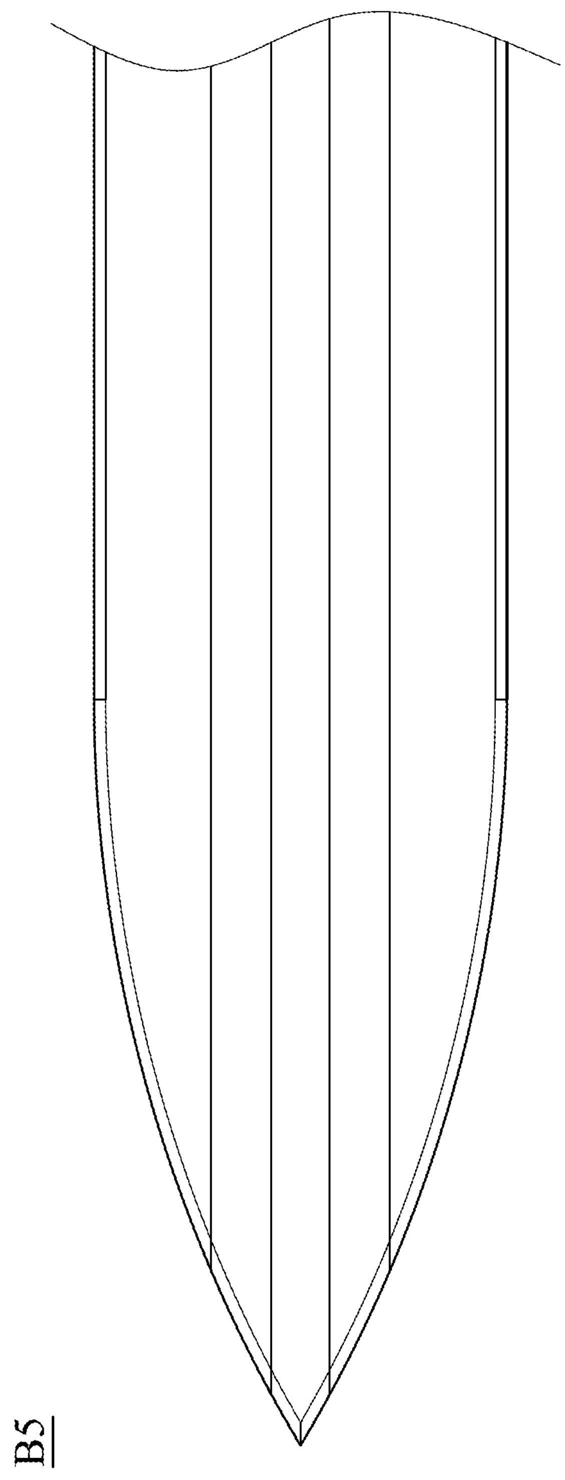
FIG. 19 shows a top view of a flat blank used for being bended and forming the insertion needle structure of the fifth embodiment of FIG. 18.

FIG. 18 shows a front section view of an insertion needle structure 5000 according to a fifth embodiment of the present disclosure. FIG. 19 shows a top view of a flat blank B5 used for being bended and forming the insertion needle structure 5000 of the fifth embodiment of FIG. 18. The insertion needle structure 5000 is similar to the insertion needle structure 1000 and includes two first inner edges 5111 and two first outer edges 5112, and each of the first inner edges 5111 is directly connected to each of the first outer edges 5112. In other words, the connecting surface 1150 of the first embodiment is omitted, and each of the first inner edges 5111 is allowed to be directly connected to each of the first outer edges 5112. In addition, the curve formed by the inclined line extending from the needle sharp portion (not labeled) of the flat blank B5 is larger than that of the flat blank B4 in the second embodiment, and the curve of the slope section can be increased.

Figure 20:
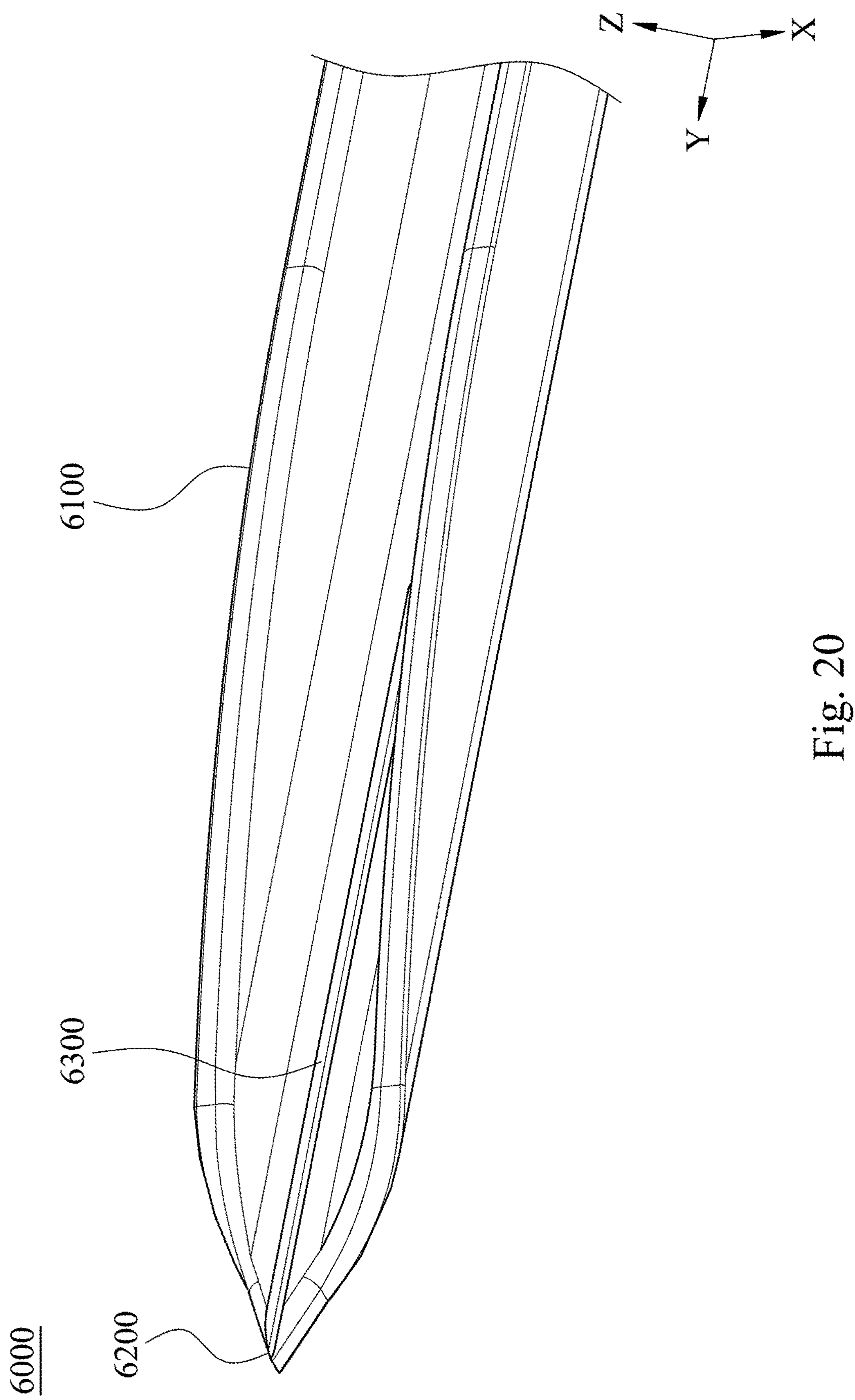
FIG. 20 shows a three-dimensional schematic view of an insertion needle structure according to a sixth embodiment of the present disclosure.

FIG. 20 shows a three-dimensional schematic view of an insertion needle structure 6000 according to a sixth embodiment of the present disclosure. The insertion needle structure 6000 is similar to the insertion needle structure 4000 of the fourth embodiment and includes a needle sharp 6200 and a needle body 6100. The difference is that the insertion needle structure 6000 can further include a reinforcing portion (not labeled). The reinforcing portion can include a groove 6300 whose manufacture process and structure are identical to that of the groove 2300 of the second embodiment, and the details will not be mentioned.

Figure 21:
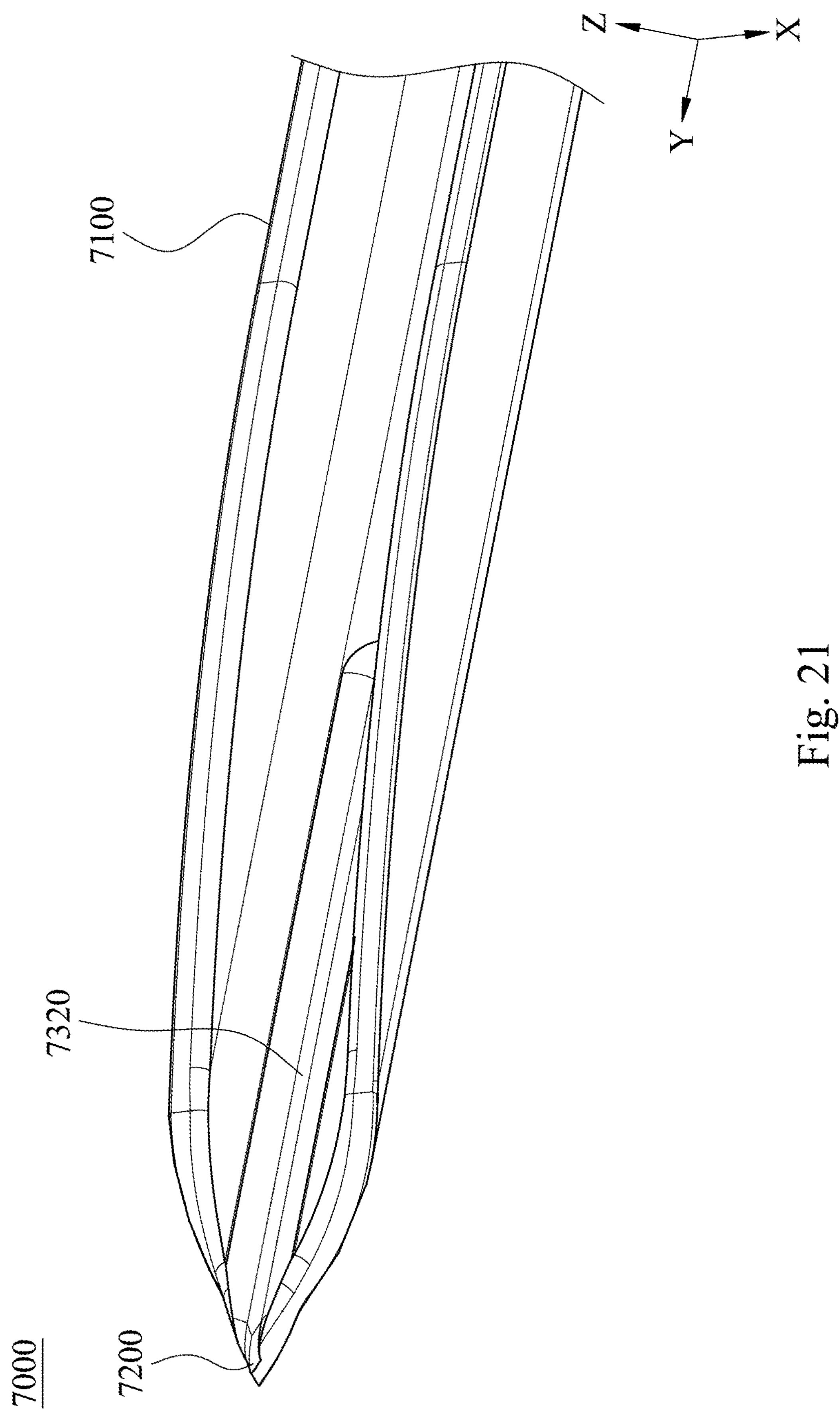
FIG. 21 shows a three-dimensional schematic view of an insertion needle structure according to a seventh embodiment of the present disclosure.
Figure 22:
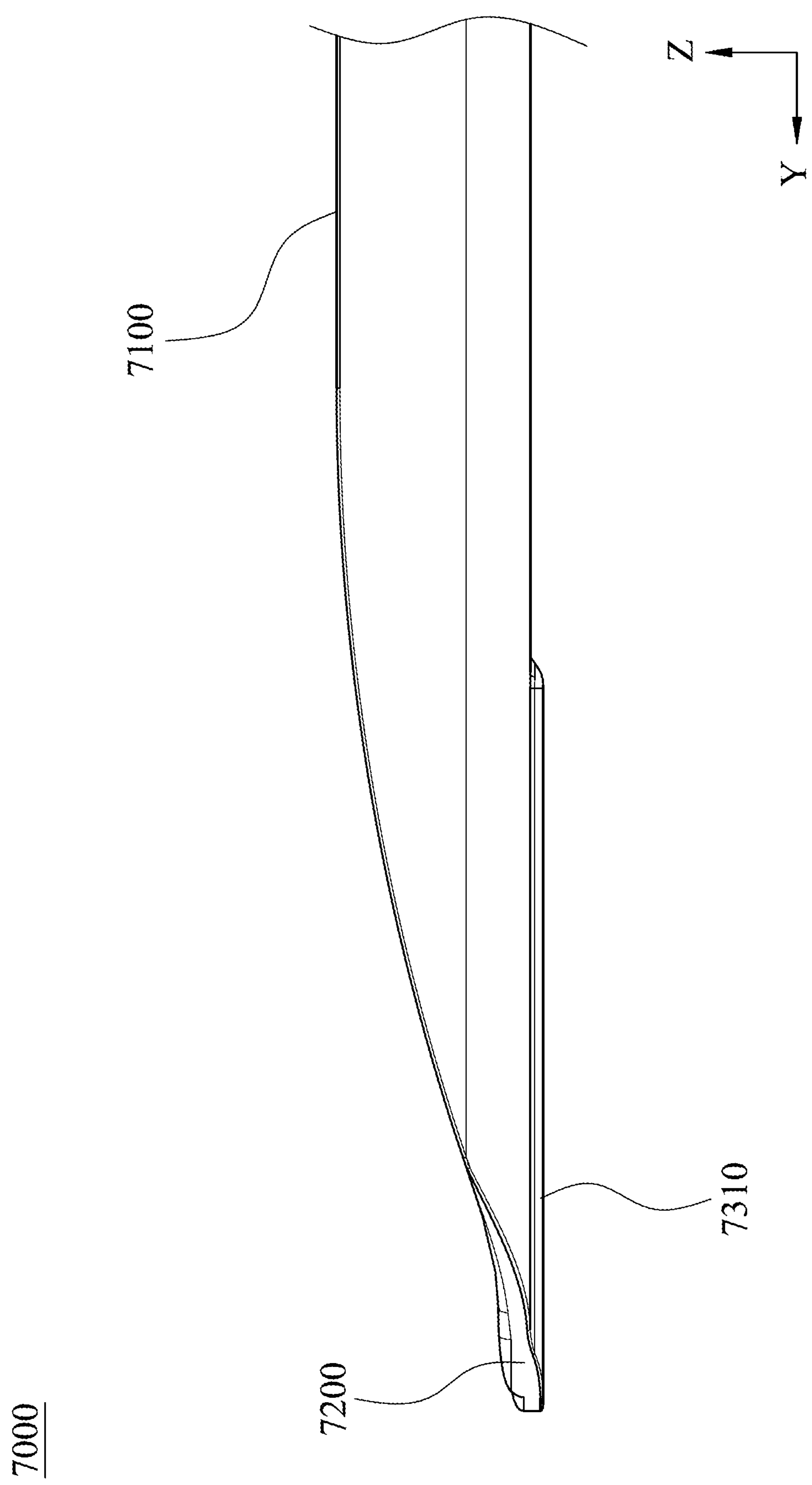
FIG. 22 shows a side view of the insertion needle structure of the seventh embodiment of FIG. 21.

FIG. 21 shows a three-dimensional schematic view of an insertion needle structure 7000 according to a seventh embodiment of the present disclosure. FIG. 22 shows a side view of the insertion needle structure 7000 of the seventh embodiment of FIG. 21. The insertion needle structure 7000 is similar to the insertion needle structure 4000 of the fourth embodiment and includes a needle sharp 7200 and a needle body 7100. The difference is that the insertion needle structure 7000 can further include a reinforcing portion (not labeled). The reinforcing portion can include a rib 7310 and a pressed depression 7320 whose manufacture processes and structures are identical to that of the rib 3310 and the pressed depression 3320 of the third embodiment, and the details will not be mentioned.

Figure 23:
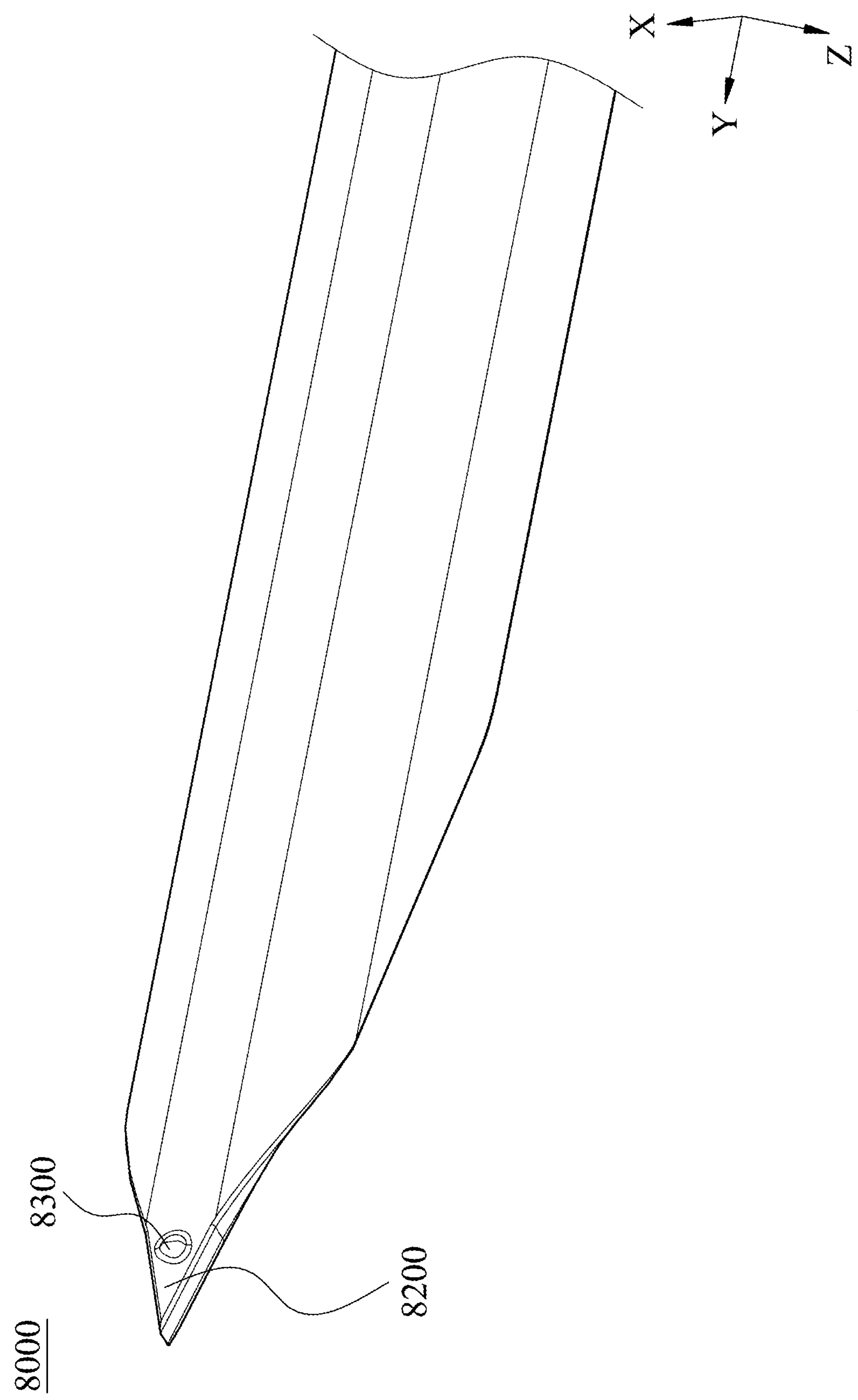
FIG. 23 shows a three-dimensional schematic view of an insertion needle structure according to an eighth embodiment of the present disclosure.

FIG. 23 shows a three-dimensional schematic view of an insertion needle structure 8000 according to an eighth embodiment of the present disclosure. The insertion needle structure 8000 is similar to the insertion needle structure 3000 of the third embodiment. The difference is that the reinforcing portion is a projection 8300 protruding from the second surface of the needle sharp 8200 facing away from the receiving space, and the projection 8300 is only located on the needle sharp 8200. The manufacture process and structure of the projection 8300 are identical to that of the rib 3310 and the pressed depression 3320 of the third embodiment, and the details will not be mentioned.

Figure 24:
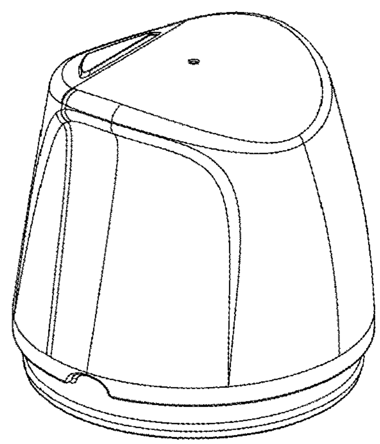
FIG. 24 shows an exploded three-dimensional schematic view of an inserter according to a ninth embodiment of the present disclosure.
Figure 24:
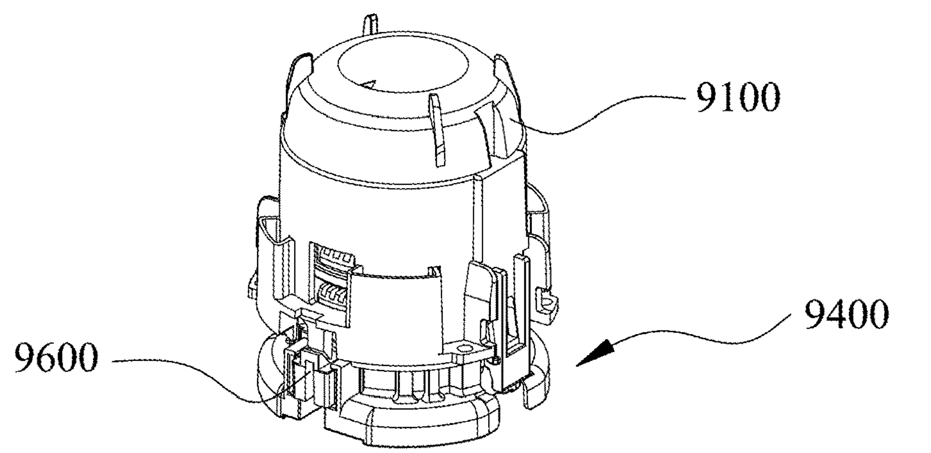
Figure 24:
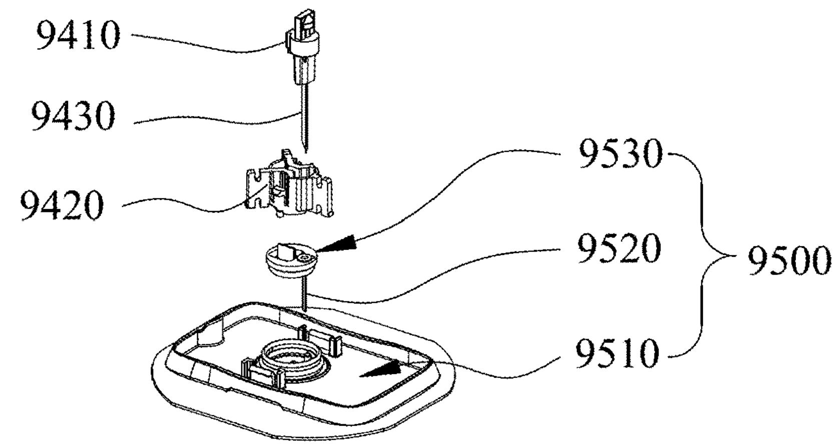
Figure 24:
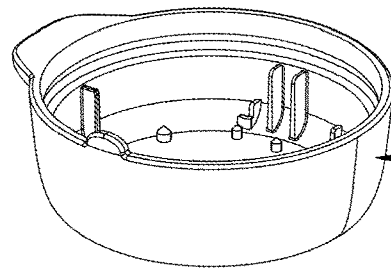
Figure 25:
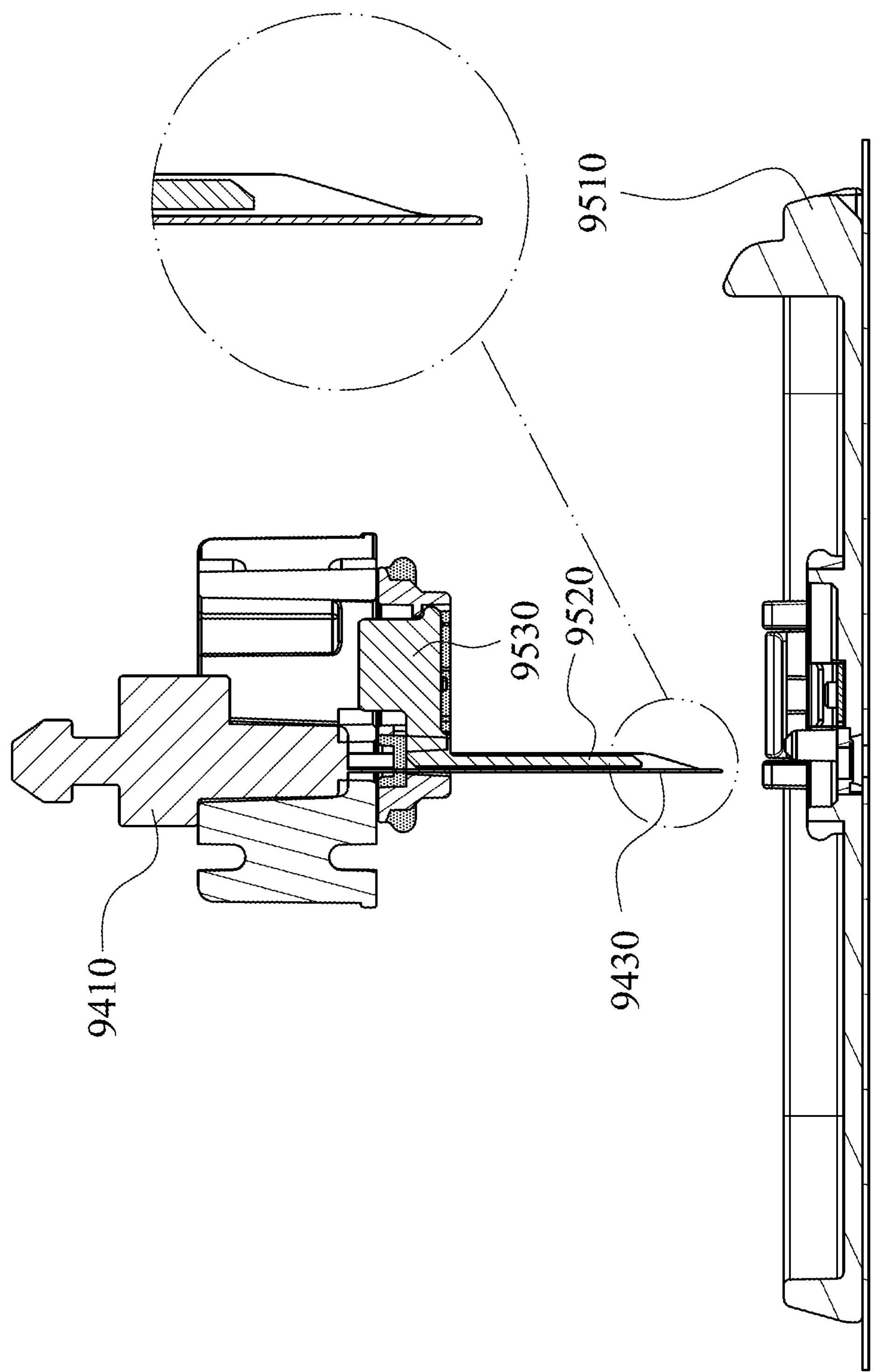
FIG. 25 shows a partial section view of the inserter of the ninth embodiment of FIG. 24.

FIG. 24 shows an exploded three-dimensional schematic view of an inserter 9000 according to a ninth embodiment of the present disclosure. FIG. 25 shows a partial section view of the inserter 9000 of the ninth embodiment of FIG. 24. The inserter 9000 includes a cover 9100, an inserting module 9400 and a removing module 9500.

The cover 9100 has a main space (not labeled). The inserting module 9400 is disposed within the main space of the cover 9100 and includes an insertion needle structure 9430. The removing module 9500 can include a base 9510 and a biosensor 9520. The base 9510 is detachably limited within the inserting module 9400. The biosensor 9520 is detachably assembled with the base 9510 and at least a part thereof is received in the receiving space (not shown in the ninth embodiment) of the insertion needle structure 9430. When the cover 9100 is pressed downward, the inserting module 9400 is driven to allow the insertion needle structure 9430 to move downward so as to carry the biosensor 9520 to be implanted underneath a skin surface of an organism for conducting a measurement of a physiological signal inside the organism.

The inserter 9000 can further include an upper cap 9200, a lower cap 9300 and two fixing member 9600. A sealing space for receiving the cover 9100, the inserting module 9400 and the removing module 9500 is formed after the upper cap 9200 is engaged with the lower cap 9300. The two fixing member 9600 is symmetrically inserted into the inserting module 9400 to be detachably coupled to the base 9510. Each of the fixing members 9600 can include a supporting portion (not shown) for supporting a biosensor bracket 9530, and the biosensor bracket 9530 is configured to carry the biosensor 9520. The inserting module 9400 can further include an insertion needle member 9410 and an insertion needle supporting socket 9420. The insertion needle member 9410 is inserted into the insertion needle supporting socket 9420, and the insertion needle structure 9430 can be assembled with the insertion needle member 9410. The insertion needle structure 9430 can be any one of the insertion needle structures 1000, 2000, 3000, 4000, 5000, 6000, 7000 and 8000, and the present disclosure is not limited thereto.

During the operation, the user can press the upper cap 9200 downward to allow the cover 9100 inside the upper cap 9200 to move downward, which causes the fixing member 9600 to horizontally move so as to release the restriction between the fixing member 9600, the biosensor bracket 9530 and the base 9510. Moreover, through release of the prepressing elasticity of a first elastic member (not shown) inside the inserting module 9400, the insertion needle member 9410, the insertion needle structure 9430 and the biosensor 9520 can be implanted underneath the skin surface of the organism. Meanwhile, the biosensor bracket 9530 is assembled with the base 9510, and the biosensor 9520 is remained under the skin surface of the organism. After release of the prepressing elasticity of a second elastic member (not shown) inside the inserting module 9400, the insertion needle member 9410 can be retraced, thereby completing automatically implanting and retracing the insertion needle member 9410.

Although the present disclosure has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present disclosure without departing from the scope or spirit of the disclosure. In view of the foregoing, it is intended that the present disclosure covers modifications and variations of this disclosure provided they fall within the scope of the following claims.

What is claimed is:

1. An insertion needle structure, which is formed by bending a flat blank and is configured for receiving and allowing a biosensor to be partially implanted underneath a skin surface of an organism, the insertion needle structure comprising:

a needle sharp; and a needle body integrally connected to the needle sharp and having a receiving space for receiving the biosensor, the needle body comprising:

a base wall;

two side walls located at two sides of the base wall, respectively, each of the side walls having a first inner edge and a first outer edge, the first inner edge near the receiving space, the first outer edge facing away from the receiving space; and two slope sections located at the two sides of the base wall, respectively, each of the slope sections connected between each of the side walls and the needle sharp, each of the slope sections being curved, each of the slope sections having a second inner edge connected to the first inner edge, and a second outer edge connected to the first outer edge; and a reinforcing portion disposed at at least one segment of a reinforcing area, wherein the reinforcing area is defined as the needle sharp and a part of the needle body adjacent to the needle sharp, the reinforcing portion is constructed by forming at least one depression structure and/or at least one protrusion structure at the at least one segment to avoid the needle sharp from bending or deforming by a force during an implanting process;

wherein each of the first inner edges, each of the second inner edges, each of the first outer edges and each of the second outer edges are curved, R11 represents a radius of each of the first inner edges, R12 represents a radius of each of the first outer edges, and a condition of $R11>R12$ is satisfied.

2. The insertion needle structure of claim 1, wherein the reinforcing portion comprises a groove extending from the needle sharp toward the base wall of the needle body.

3. The insertion needle structure of claim 1, wherein the reinforcing portion comprises a rib extending from the needle sharp toward the base wall of the needle body.

4. The insertion needle structure of claim 1, wherein the flat blank has a thickness represented by T1, and a condition of $20\% \leq R11/T1 \leq 50\%$ is satisfied.

5. The insertion needle structure of claim 1, wherein the needle sharp comprises two slants connected to the two slope sections, respectively, the two slants intersect at a needle tip, each of the slants comprises:

a needle sharp top edge being curved and connected to one of the two second inner edges; and a needle sharp bottom edge being curved and connected to one of the two second outer edges;

wherein R31 represents a radius of each of the needle sharp top edges, R32 represents a radius of each of the needle sharp bottom edges, and a condition of $R31>R32$ is satisfied.

6. The insertion needle structure of claim 5, wherein each of the first outer edges, each of the second outer edges, and each of the needle sharp bottom edges are formed as the flat blank stamped and elastic deformed from a sheet.

7. The insertion needle structure of claim 5, wherein L1 represents a needle sharp length defined by a distance along a length direction between the needle tip and a stop position of each of the slants, L2 represents an expanding length defined by a distance along the length direction between the needle tip and a stop position of each of the slope sections, and a condition of $L1/L2 \leq 15\%$ is satisfied.

8. An insertion needle structure, which is formed by bending a flat blank and is configured for receiving and allowing a biosensor to be partially implanted underneath a skin surface of an organism, the insertion needle structure comprising:

a needle sharp; and a needle body integrally connected to the needle sharp and having a receiving space for receiving the biosensor, the needle body comprising:

a base wall;

two side walls located at two sides of the base wall, respectively, each of the side walls having a first inner edge and a first outer edge, the first inner edge near the receiving space, the first outer edge facing away from the receiving space; and two slope sections located at the two sides of the base wall, respectively, each of the slope sections connected between each of the side walls and the needle sharp, each of the slope sections being curved, each of the slope sections having a second inner edge connected to the first inner edge, and a second outer edge connected to the first outer edge;

wherein each of the first inner edges, each of the second inner edges, each of the first outer edges and each of the second outer edges are curved, R11 represents a radius of each of the first inner edges, R12 represents a radius of each of the first outer edges, and a condition of $R11>R12$ is satisfied.

9. The insertion needle structure of claim 8, wherein the flat blank has a thickness represented by T1, and a condition of $20\% \leq R11/T1 \leq 50\%$ is satisfied.

10. The insertion needle structure of claim 8, wherein a condition of $3 \leq R11/R12 \leq 10$ is satisfied.

11. The insertion needle structure of claim 8, wherein the needle sharp comprises two slants connected to the two slope sections, respectively, the two slants intersect at a needle tip, L1 represents a needle sharp length defined by a distance along a length direction between the needle tip and a stop position of each of the slants, L2 represents an expanding length defined by a distance along the length direction between the needle tip and a stop position of each of the slope sections, and a condition of $L1/L2 \leq 15\%$ is satisfied.

12. The insertion needle structure of claim 8, wherein each of the first outer edges and each of the second outer edges are formed as the flat blank stamped and elastic deformed from a sheet.

13. An insertion needle structure, which is formed by bending a flat blank and is configured for receiving and allowing a biosensor to be partially implanted underneath a skin surface of an organism, the insertion needle structure comprising:

a needle sharp; and a needle body integrally connected to the needle sharp and having a receiving space for receiving the biosensor, the needle body comprising:

a base wall;

two side walls located at two sides of the base wall, respectively, each of the side walls having a first inner edge and a first outer edge, the first inner edge near the receiving space, the first outer edge facing away from the receiving space; and two slope sections located at the two sides of the base wall, respectively, each of the slope sections connected between each of the side walls and the needle sharp, each of the slope sections having a second inner edge connected to the first inner edge, and a second outer edge connected to the first outer edge;

wherein each of the first inner edges, each of the second inner edges, each of the first outer edges and each of the second outer edges are curved, R11 represents a radius of each of the first inner edges, R12 represents a radius of each of the first outer edges, and a condition of $R11>R12$ is satisfied.

14. The insertion needle structure of claim 13, wherein the flat blank has a thickness represented by T1, and a condition of $20\%\ R11/T1 \leq 50\%$ is satisfied.

15. The insertion needle structure of claim 13, wherein a condition of $3 \leq R11/R12 \leq 10$ is satisfied.

16. The insertion needle structure of claim 13, wherein R21 represents a radius of each of the second inner edges, and R22 represents a radius of each of the second outer edges, and conditions of $R11=R21$ and $R12=R22$ are satisfied.

17. The insertion needle structure of claim 13, wherein the needle sharp comprises two slants connected to the two slope sections, respectively, the two slants intersect at a needle tip with an angle contained therebetween, each of the slants comprises:

a needle sharp top edge being curved and connected to one of the two second inner edges; and a needle sharp bottom edge being curved and connected to one of the two second outer edges;

wherein R31 represents a radius of each of the needle sharp top edges, R32 represents a radius of each of the needle sharp bottom edges, and a condition of $R31>R32$ is satisfied.

18. The insertion needle structure of claim 17, wherein the angle is within a range from 20 degrees to 40 degrees.

19. The insertion needle structure of claim 13, wherein the needle body further comprises two curved connecting sections, each of the curved connecting sections is connected between each of the side walls and the base wall and between each of the slope sections and the base wall, each of the curved connecting sections has a height thereof represented by T2 along a height direction of the insertion needle structure, the flat blank has a thickness represented by T1, and a condition of $T2/T1 \geq 1.5$ is satisfied.

20. The insertion needle structure of claim 13, wherein the needle body further comprises:

a connecting surface parallel to a width direction of the insertion needle structure and connected between each of the first inner edges and each of the first outer edges.

21. The insertion needle structure of claim 13, wherein each of the first inner edges is directly connected to each of the first outer edges.

22. The insertion needle structure of claim 13, wherein a burr height formed as the flat blank stamped from a sheet is smaller than or equal to 0.02 mm.

23. The insertion needle structure of claim 13, wherein a finishing surface is formed as the flat blank stamped from a sheet, the flat blank has a thickness represented by T1, the finishing surface has a depth represented by T3, and a condition of $T3/T1 \geq 50\%$ is satisfied.

24. An inserter, comprising:

a cover having a main space;

an inserting module disposed within the main space of the cover and comprising an insertion needle structure of claim 13; and a removing module comprising:

a base detachably limited within the inserting module; and a biosensor detachably assembled with the base and at least a part thereof received in the receiving space of the insertion needle structure;

wherein when the cover is pressed downward, the inserting module is driven to allow the insertion needle structure to move downward so as to carry the biosensor to implant underneath the skin surface of the organism for conducting a measurement of a physiological signal inside the organism.

* * * * *